(12) United States Patent
Adams et al.

(10) Patent No.: US 10,023,631 B2
(45) Date of Patent: *Jul. 17, 2018

(54) ALBUMIN BINDING ANTIBODIES AND BINDING FRAGMENTS THEREOF

(71) Applicant: UCB Biopharma SPRL, Brussels (BE)

(72) Inventors: Ralph Adams, Slough (GB); Pallavi Bhatta, Slough (GB); Sam Philip Heywood, Slough (GB); David Paul Humphreys, Slough (GB)

(73) Assignee: UCB Biopharma SPRL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/795,874

(22) Filed: Oct. 27, 2017

(65) Prior Publication Data

US 2018/0134774 A1    May 17, 2018

Related U.S. Application Data

(62) Division of application No. 14/356,181, filed as application No. PCT/EP2012/072335 on Nov. 9, 2012, now Pat. No. 9,803,004.

(60) Provisional application No. 61/558,559, filed on Nov. 11, 2011.

(51) Int. Cl.
*C07K 16/18* (2006.01)
*C07K 16/28* (2006.01)

(52) U.S. Cl.
CPC .......... *C07K 16/18* (2013.01); *C07K 16/2878* (2013.01); *C07K 2317/24* (2013.01); *C07K 2317/31* (2013.01); *C07K 2317/55* (2013.01); *C07K 2317/624* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss |
| 5,223,409 A | 6/1993 | Ladner |
| 5,403,484 A | 4/1995 | Ladner |
| 5,427,908 A | 6/1995 | Dower |
| 5,516,637 A | 5/1996 | Huang |
| 5,545,806 A | 8/1996 | Lonberg |
| 5,569,825 A | 10/1996 | Lonberg |
| 5,571,698 A | 11/1996 | Ladner |
| 5,580,717 A | 12/1996 | Dower |
| 5,585,089 A | 12/1996 | Queen |
| 5,625,126 A | 4/1997 | Lonberg |
| 5,633,425 A | 5/1997 | Lonberg |
| 5,658,727 A | 8/1997 | Barbas |
| 5,661,016 A | 8/1997 | Lonberg |
| 5,677,425 A | 10/1997 | Bodmer |
| 5,698,426 A | 12/1997 | Huse |
| 5,733,743 A | 3/1998 | Johnson |
| 5,750,753 A | 5/1998 | Kimae |
| 5,770,429 A | 6/1998 | Lonberg |
| 5,780,225 A | 7/1998 | Wigler |
| 5,821,047 A | 10/1998 | Garrard |
| 5,969,108 A | 10/1999 | McCafferty |
| 6,267,964 B1 | 7/2001 | Nygren |
| 6,331,415 B1 | 12/2001 | Cabilly |
| 6,642,356 B1 | 11/2003 | Humphreys |

FOREIGN PATENT DOCUMENTS

| | | |
|---|---|---|
| EP | 0368684 | 3/1994 |
| EP | 0486525 | 6/1994 |
| EP | 0438474 | 5/1996 |
| EP | 0463151 | 6/1996 |
| EP | 0546073 | 9/1997 |
| EP | 0656946 | 3/2010 |
| WO | 199002809 | 3/1990 |
| WO | 199109967 | 7/1991 |
| WO | 1991010737 | 7/1991 |
| WO | 199201047 | 1/1992 |
| WO | 1992002551 | 2/1992 |
| WO | 1992018619 | 10/1992 |

(Continued)

OTHER PUBLICATIONS

Holt et al. (Protein Engineering, Design, and Selection, 21(5): 283-288, 2008).*
Adair, J.R., et al., "Therapeutic antibodies," Drug Design Reviews—Online, 2005, vol. 2, No. 3, pp. 209-217.
Alfthan, Kaija et al., "Properties of a single-chain antibody containing different linker peptides," Prot. Eng., vol. 8, No. 7, pp. 725-731 (1995).
Ames, R.S., et al., "Conversion of Murine Fabs Isolated from a Combinatorial Phage Display Library to Full Length Immunoglobulins," J. Immunol. Methods, vol. 184, No, 2, pp. 177-186, 1995.
Angal, S., et al. "A single amino acid substitution abolishes the heterogeneity of chimeric mouse/human (IgG4) antibody", Molecular Immunology, vol. 30, No. 1, pp. 105-108, 1993.

(Continued)

*Primary Examiner* — Nelson B Moseley, II
(74) *Attorney, Agent, or Firm* — Saul Ewing Arnstein & Lehr LLP

(57) ABSTRACT

A serum albumin binding antibody or fragment thereof comprising a heavy chain variable domain having the sequence given in SEQ ID NO: 1 or SEQ ID NO:2 and/or comprising a light chain variable domain having the sequence given in SEQ ID NO:3 or SEQ ID NO:4, in particular comprising a heavy chain variable domain and a light chain variable domain having the sequence given in SEQ ID NO: 1 and SEQ ID NO:3 or a heavy chain variable domain and a light chain variable domain having the sequence given in SEQ ID NO: 2 and SEQ ID NO:4. The disclosure also extends to polynucleotides encoding the antibodies or fragments, vectors comprising same and host cells capable of expressing the polynucleotides. The disclosure further includes pharmaceutical compositions comprising the antibodies or fragments and therapeutic used of any one of the same.

3 Claims, 10 Drawing Sheets

(56) References Cited

FOREIGN PATENT DOCUMENTS

Figure 1A:
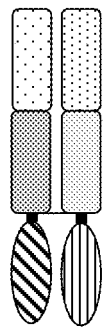

| WO | 1992022583 | 12/1992 |
|---|---|---|
| WO | 1993011236 | 6/1993 |
| WO | 1995015982 | 6/1995 |
| WO | 1995020401 | 8/1995 |
| WO | 1997034631 | 9/1997 |
| WO | 1998025971 | 6/1998 |
| WO | 1998037200 | 8/1998 |
| WO | 1999015549 | 4/1999 |
| WO | 1999037791 | 7/1999 |
| WO | 1999064460 | 12/1999 |
| WO | 2001045746 | 6/2001 |
| WO | 2002076489 | 10/2002 |
| WO | 2004001064 | 12/2003 |
| WO | 2004003019 | 1/2004 |
| WO | 2004051268 | 6/2004 |
| WO | 2004106377 | 12/2004 |
| WO | 2005003169 | 1/2005 |
| WO | 2005003170 | 1/2005 |
| WO | 2005003171 | 1/2005 |
| WO | 2005113605 | 12/2005 |
| WO | 2005118642 | 12/2005 |
| WO | 2006059105 | 6/2006 |
| WO | 2006106323 | 10/2006 |
| WO | 2008096158 | 8/2008 |
| WO | 2009040562 | 4/2009 |
| WO | 2010035012 | 4/2010 |
| WO | 2010096418 | 8/2010 |
| WO | 2011006915 | 1/2011 |
| WO | 2011030107 A1 | 3/2011 |
| WO | 2011036460 | 3/2011 |
| WO | 2011061492 A2 | 5/2011 |
| WO | 2011086091 | 7/2011 |

OTHER PUBLICATIONS

Babcook, J., et al., "A novel strategy for generating monoclonal antibodies from single, isolated lymphocytes producing antibodies of defined specificities," Proc. Natl. Acad. Sci. USA, vol. 93, No. 15, pp. 7843-7848, 1996.

Bird, R.E., et al., "Single-chain antigen-binding proteins," Science, vol. 242, No. 4877, pp. 423-426, 1988.

Brinkmann, U., et al., "Phage Display of Disulfide-Stabilized FV Fragments," J. Immunol. Methods, vol. 182, No. 1, pp. 41-50, 1995.

Burton, D.R., et al., "Human Antibodies from Combinatorial Libraries," Advances in Immunology, vol. 57, pp. 191-280, 1994.

Cole, S.P.C., et al., "The EBV-hybridoma technique and its application to human lung cancer," Monoclonal Antibodies and Cancer Therapy, vol. 27, (UCLA Symposia on Molecular and Cellular Biology, New Series, R.A. Reisfeld and S. Sell (eds.)), pp. 77-96, Alan R. Liss, Inc., N.Y., 1985.

Crameri, A., et al., "DNA shuffling of a family of genes from diverse species accelerates directed evolution," Nature, Jan. 15, 1998, vol. 391, pp. 288-291.

Harris, R.J., "Processing of C-terminal lysine and arginine residues of proteins isolated from mammalian cell culture," Journal of Chromatography, vol. 705, No. 1, pp. 129-134, 1995.

Holliger, P., et al., "Engineered antibody fragments and the rise of single domains," Nature Biotechnology, vol. 23, No. 9, pp. 1126-1136, Sep. 2005.

Holt, L. J., "Domain Antibodies: Proteins for Therapy," Trends in Biotechnology, Elsevier Publications, Cambridge, GB, vol. 21, No. 11, pp. 484-490, 2003.

Holt, L.J. et al., "Anti-serum albumin domain antibodies for extending the half-lives of short lived drugs," Protein Engineering, Design and Selection, Oxford Journal, London, GB, vol. 21 (2008), pp. 283-288.

Humphreys, D.P., et al., "A plasmid system for optimization of Fab production in *Escherichia coli*: importance of balance of heavy chain and light chain synthesis", Protein Expression and Purification, vol. 26, No. 2, pp. 309-320, 2002.

Huston et al., "Protein engineering of antibody binding sites: recovery of specific activity in an anti-digoxin single-chain Fv analogue produced in *Escherichia coli*," PNAS, vol. 85, No. 16, pp. 5879-5883 (1988).

International Search Report based on International Application No. PCT/EP2012/072335 dated Apr. 22, 2013.

Jespers et al., "Aggregation-resistant domain antibodies selected on phage by heat denaturation," Nature Biotechnology, vol. 22, No. 9, pp. 1161-1165, Sep. 2004.

Kettleborough, C.A., et al., "Isolation of tumor cell-specific single-chain Fv from immunized mice using phage-antibody libraries and the reconstruction of whole antibodies from these antibody fragments," Eur. J. Immunol., vol. 24, No. 4, pp. 952-958, 1994.

Kohler, G. et al., Continuous cultures of fused cells secreting antibody of predefined specificity, Nature, Aug. 7, 1975, pp. 495-497, vol. 256, nature Publishing Group.

Kostelny et al., "Formation of a bispecific antibody by the use of leucine zippers," J. Immunol., vol. 148, No. 5, pp. 1547-1553, Mar. 1, 1992.

Kozbor, D., et al., "The production of monoclonal antibodies from human lymphocytes," Immunology Today, vol. 4, No. 3, pp. 72-79, 1983.

Low, Nigel M. et al., "Mimicking somatic hypermutation: affinity maturation of antibodies displayed on bacteriophage using a bacterial mutator strain", J. Mol. Biol., vol. 260, pp. 359-368, 1996.

Luo et al., "VI-Linker-Vh Orientation-Dependent Expression of Single Chain Fv Containing an Engineered Disulfide-Stabilized Bond in the Framework Region," J. Biochem., vol. 118, No. 4, pp. 825-831 (1995).

Marks, J.D., et al., "By-passing Immunization Human: Building High Affinity Human Antibodies by Chain Shuffling," Bio/Technology, vol. 10, pp. 779-783, 1992.

Medasan et al., "Delineation of the amino acid residues involved in transcytosis and catabolism of mouse IgG1," J. Immunol., vol. 158, No. 5, pp. 2211-2217, Mar. 1, 1997.

Mountain, A., et al., "Engineering antibodies for therapy," Biotechnol. Genet. Eng. Rev., vol. 10, pp. 1-142, 1992.

Nguyen, A. et al., "The pharmacokinetics of an albumin-binding Fab (AB.Fab) can be modulated as a function of affinity for albumin," Protein Engineering, Design & Selection, vol. 19, No. 7, pp. 291-297 (2006).

Orlandi, et al., 'Cloning immunoglobulin variable domains for expression by the polymerase chain reaction', PNAS USA, vol. 86, pp. 3833-3837, May 1989.

Patten, P., et al., "Applications of DNA shuffling to pharmaceuticals and vaccines," Curr. Opin. Biotechnol., vol. 8, No. 6, pp. 724-733, 1997.

Persic, L., et al., "An integrated vector system for the eukaryotic expression of antibodies or their fragments after selection from phage display libraries," Gene, vol. 187, No. 1, pp. 9-18, 1997.

Peters et al., "Serum albumin," Adv. Protein Chem, vol. 37, pp. 161-245 (1985).

Related U.S. Appl. No. 14/356,181, filed May 5, 2014, now U.S. Pat. No. 9,803,004, issued Oct. 31, 2017.

Richter et al., "Polyionic fusion peptides function as specific dimerization motifs," Prot. Eng., vol. 14, No. 10, pp. 775-783 (2001).

Riechmann, Lutz et al., "Reshaping Human Antibodies for Therapy," Nature, vol. 332:, pp. 323-327, Mar. 1988.

Smith, B. et al., "Prolonged in Vivo Residence Times of antibody Fragments Associated with Albumin", Bioconjugate Chem., vol. 12, pp. 750-756, 2001.

Tang et al., "Selection of Linkers for a Catalytic Single-chain Antibody Using Phage Display Technology," J. Bio. Chem., vol. 271, No. 26, pp. 15682-15686 (1996).

Thompson, J., et al., "Affinity maturation of a high-affinity human monoclonal antibody against the third hypervariable loop of human immunodeficiency virus: use of phage display to improve affinity and broaden strain reactivity," J. Mol. Biol., vol. 256, No. 1, pp. 77-88, 1996.

(56) References Cited

OTHER PUBLICATIONS

Turner et al., "Importance of the linker in expression of single-chain Fv antibody fragments:optimisation of peptide sequence using phage display technology," Journal of Immunological Methods, vol. 205, pp. 43-54 (1997).
Verma, R., et al., "Antibody engineering: comparison of bacterial, yeast, insect and mammalian expression systems," Journal of Immunological Methods, vol. 216, Nos. 1-2, pp. 165-181, 1998.
Wang et al., Antiviral Research, 80: 168-177, 2008.
Ward, E.S., et al., "Binding activities of a repertoire of single irnrnunoglobulin variable domains secreted from *Escherichia coil*," Nature, vol. 341, No. 6242, pp. 544-546, Oct. 12, 1989.
Wright et al., "Phage display of chelating recombinant antibody libraries," Mol. Immunol., vol. 44, No. 11, pp. 2860-2869 (2007).
Written Opinion of the International Searching Authority for International Application No. PCT/EP2012/072335 dated Apr. 22, 2013.
Yang, W.P. et al., 'CDR Walking Mutagenesis for the Affinity Maturation of a Potent Human Anti-HIV-1 Antibody into the Picomolar Range,' J. Mol. Biol., vol. 254, No. 3, pp. 392-403, 1995.

\* cited by examiner

First Variable region of light chain VL1

First Variable region of heavy chain VH1

Constant regions cKappa and CH1

Second variable region of light chain VL2

Second variable region of heavy chain VH2

Disulphide bond

Figure 2

(a) Heavy chain variable domain of anti-albumin antibody (no ds) (SEQ ID NO:1)
EVQLLESGGGLVQPGGSLRLSCAVSGIDLSNYAINWVRQAPGKGLEWIGIIWASGTTFYATWAKGRFTI
SRDNSKNTVYLQMNSLRAEDTAVYYCARTVPGYSTAPYFDLWGQGTLVTVSS (b) Heavy chain variable domain of anti-albumin antibody (ds) (SEQ ID NO:2)
EVQLLESGGGLVQPGGSLRLSCAVSGIDLSNYAINWVRQAPGKCLEWIGIIWASGTTFYATWAKGRFTI
SRDNSKNTVYLQMNSLRAEDTAVYYCARTVPGYSTAPYFDLWGQGTLVTVSS (c) Light chain variable domain of anti-albumin antibody (no ds) (SEQ ID NO:3)
DIQMTQSPSSVSASVGDRVTITCQSSPSVWSNFLSWYQQKPGKAPKLLIYEASKLTSGVPSRFSGSGSG
TDFTLTISSLQPEDFATYYCGGGYSSISDTTFGGGTKVEIKRT (d) Light chain variable domain of anti-albumin antibody (ds) (SEQ ID NO:4)
DIQMTQSPSSVSASVGDRVTITCQSSPSVWSNFLSWYQQKPGKAPKLLIYEASKLTSGVPSRFSGSGSG
TDFTLTISSLQPEDFATYYCGGGYSSISDTTFGCGTKVEIKRT (e) Linker 1 (SEQ ID NO:5)
SGGGGSGGGGTGGGGS (f) Linker 2 (SEQ ID NO:6)
GGGGSGGGGSGGGGS (g) A26 Fab Heavy-(G4S,G4T,G4S)-645dsFv(gH5) (SEQ ID NO:7)
EVQLVESGGGLVQPGGSLRLSCAASGFTFTNYGIHWIRQAPGKGLEWVASISPSGGLTYYRDSVKGRFT
ISRDDAKNSPYLQMNSLRAEDTAVYYCATGGEGIFDYWGQGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCSGGGGSGGGGTGGGGSEVQLLESGGGLVQPGGSLRLSCAVSGIDLSNYAINWVRQA
PGKCLEWIGIIWASGTTFYATWAKGRFTISRDNSKNTVYLQMNSLRAEDTAVYYCARTVPGYSTAPYFD
LWGQGTLVTVSS (h) A26 Fab Light-(3xG4S)-645dsFv(gL4) (SEQ ID NO:8)
DIQMTQSPSSLSASVGDRVTITCRATQSIYNALAWYQQKPGKAPKLLIYNANTLHTGVPSRFSASGSGT
DSTLTISSLQPEDFATYYCQQYYDYPLTFGGGTKVEIKRTVAAPSVFIFPPSDEQLKSGTASVVCLLNN
FYPREAKVQWKVDNALQSGNSQESVTEQDSKDSTYSLSSTLTLSKADYEKHKVYACEVTHQGLSSPVTK
SFNRGECGGGGSGGGGSGGGGSDIQMTQSPSSVSASVGDRVTITCQSSPSVWSNFLSWYQQKPGKAPKL
LIYEASKLTSGVPSRFSGSGSGTDFTLTISSLQPEDFATYYCGGGYSSISDTTFGCGTKVEIKRT

FIGURE 3

645gH1 heavy chain variable domain (SEQ ID NO: 9)
EVQLLESGGGLVQPGGSLRLSCAVSGIDLSNYAINWVRQAPGKCLEWIGIIWASGTTFYATWAKGRFTI
SRDSTTVYLQMNSLRAEDTAVYYCARTVPGYSTAPYFDLWGQGTLVTVSS 645gL1 light chain variable domain (SEQ ID NO: 10)
DIVMTQSPSSVSASVGDRVTITCQSSPSVWSNFLSWYQQKPGKAPKLLIYEASKLTSGVPSRFKGSGSG
TDFTLTISSLQPEDFATYYCGGGYSSISDTTFGCGTKVEIK A26 Fab Heavy-(3xG4S)-645dsFv(gH1) (SEQ ID NO:11)
EVQLVESGGGLVQPGGSLRLSCAASGFTFTNYGIHWIRQAPGKGLEWVASISPSGGLTYYRDSVKGRFT
ISRDDAKNSPYLQMNSLRAEDTAVYYCATGGEGIFDYWGQGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCSGGGGSGGGGSGGGGSEVQLLESGGGLVQPGGSLRLSCAVSGIDLSNYAINWVRQA
PGKCLEWIGIIWASGTTFYATWAKGRFTISRDSTTVYLQMNSLRAEDTAVYYCARTVPGYSTAPYFDLW
GQGTLVTVSS A26 Fab Light-(3xG4S)-645dsFv(gL1) (SEQ ID NO:12)
DIQMTQSPSSLSASVGDRVTITCRATQSIYNALAWYQQKPGKAPKLLIYNANTLHTGVPSRFSASGSGT
DSTLTISSLQPEDFATYYCQQYYDYPLTFGGGTKVEIKRTVAAPSVFIFPPSDEQLKSGTASVVCLLNN
FYPREAKVQWKVDNALQSGNSQESVTEQDSKDSTYSLSSTLTLSKADYEKHKVYACEVTHQGLSSPVTK
SFNRGECSGGGGSGGGGSGGGGSDIVMTQSPSSVSASVGDRVTITCQSSPSVWSNFLSWYQQKPGKAPK
LLIYEASKLTSGVPSRFKGSGSGTDFTLTISSLQPEDFATYYCGGGYSSISDTTFGCGTKVEIK

FIGURE 4

645 gH5gL4 (SEQ ID NO: 13)
GAGGTTCAGCTGCTGGAGTCTGGAGGCGGGCTTGTCCAGCCTGGAGGGAGCCTGCGTCTCTCTTGTGCA
GTAAGCGGCATCGACCTGTCCAACTACGCGATTAACTGGGTACGTCAGGCACCGGGTAAAGGTCTGGAA
TGGATCGGCATCATCTGGGCCTCTGGTACGACCTTCTACGCTACTTGGGCCAAAGGTCGTTTCACCATC
TCCCGTGACAACTCTAAAAACACCGTGTACCTGCAGATGAACTCTCTGCGTGCGGAAGACACTGCGGTT
TACTATTGCGCGCGTACCGTTCCGGGCTATTCTACTGCACCGTACTTCGACCTGTGGGGTCAGGGTACT
CTGGTTACCGTCTCGAGTGGAGGTGGCGGTTCTGGCGGTGGCGGTTCCGGTGGCGGTGGATCGGAGGT
GGCGGTTCTGATATCCAGATGACCCAGAGTCCAAGCAGTGTTTCCGCCAGCGTAGGCGATCGTGTGACT
ATTACCTGTCAGTCCTCTCCGAGCGTTTGGTCCAACTTCCTGAGCTGGTACCAGCAGAAACCGGGTAAA
GCCCCGAAACTGCTGATCTACGAGGCGTCTAAACTGACCTCTGGTGTACCGTCCCGTTTCTCTGGCTCT
GGCTCTGGTACGGACTTCACTCTGACCATCTCCTCTGCAGCCGGAAGACTTTGCAACGTACTACTGC
GGTGGTGGTTACTCTTCCATCTCTGACACCACGTTCGGTGGAGGCACCAAAGTTGAAATCAAACGTACG
CATCACCATCACCATCACCATCAC 645 gH5gL4 (SEQ ID NO: 14)
EVQLLESGGGLVQPGGSLRLSCAVSGIDLSNYAINWVRQAPGKGLEWIGIIWASGTTFYATWAKGRFTI
SRDNSKNTVYLQMNSLRAEDTAVYYCARTVPGYSTAPYFDLWGQGTLVTVSSGGGGSGGGGSGGGGSGG
GGSDIQMTQSPSSVSASVGDRVTITCQSSPSVWSNFLSWYQQKPGKAPKLLIYEASKLTSGVPSRFSGS
GSGTDFTLTISSLQPEDFATYYCGGGYSSISDTTFGGGTKVEIKRTHHHHHHHHHH 645 gH5gL4ds (SEQ ID NO: 15)
GAGGTTCAGCTGCTGGAGTCTGGAGGCGGGCTTGTCCAGCCTGGAGGGAGCCTGCGTCTCTCTTGTGCA
GTAAGCGGCATCGACCTGTCCAACTACGCGATTAACTGGGTACGTCAGGCACCGGGTAAATGCCTGGAA
TGGATCGGCATCATCTGGGCCTCTGGTACGACCTTCTACGCTACTTGGGCCAAAGGTCGTTTCACCATC
TCCCGTGACAACTCTAAAAACACCGTGTACCTGCAGATGAACTCTCTGCGTGCGGAAGACACTGCGGTT
TACTATTGCGCGCGTACCGTTCCGGGCTATTCTACTGCACCGTACTTCGACCTGTGGGGTCAGGGTACT
CTGGTTACCGTCTCGAGTGGAGGTGGCGGTTCTGGCGGTGGCGGTTCCGGTGGCGGTGGATCGGAGGT
GGCGGTTCTGATATCCAGATGACCCAGAGTCCAAGCAGTGTTTCCGCCAGCGTAGGCGATCGTGTGACT
ATTACCTGTCAGTCCTCTCCGAGCGTTTGGTCCAACTTCCTGAGCTGGTACCAGCAGAAACCGGGTAAA
GCCCCGAAACTGCTGATCTACGAGGCGTCTAAACTGACCTCTGGTGTACCGTCCCGTTTCTCTGGCTCT
GGCTCTGGTACGGACTTCACTCTGACCATCTCCTCTGCAGCCGGAAGACTTTGCAACGTACTACTGC
GGTGGTGGTTACTCTTCCATCTCTGACACCACGTTCGGTTGTGGCACCAAAGTTGAAATCAAACGTACG
CATCACCATCACCATCACCATCAC 645 gH5gL4ds (SEQ ID NO: 16)
EVQLLESGGGLVQPGGSLRLSCAVSGIDLSNYAINWVRQAPGKCLEWIGIIWASGTTFYATWAKGRFTI
SRDNSKNTVYLQMNSLRAEDTAVYYCARTVPGYSTAPYFDLWGQGTLVTVSSGGGGSGGGGSGGGGSGG
GGSDIQMTQSPSSVSASVGDRVTITCQSSPSVWSNFLSWYQQKPGKAPKLLIYEASKLTSGVPSRFSGS
GSGTDFTLTISSLQPEDFATYYCGGGYSSISDTTFGCGTKVEIKRTHHHHHHHHHH

FIGURE 5

LINKER (SEQ ID NO: 17)
GGGGSGGGGSGGGGSGGGGS

LINKER (SEQ ID NO. 18)
SGGGGSGGGGSGGGGS cKappa (SEQ ID NO. 19)
VAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC CH1 (SEQ ID NO. 20)
ASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSC A26-645gH5gL4 Transient expression of FabA-dsscFv in HEK293 cell line SDS-PAGE of purified FabA-dsscFv (HEK293)

FIGURE 9

Affinity to HSA and AntigenA binding (HEK293)

| | Analyte | | Concentrations used | ka (1/Ms) | kd (1/s) | KD (M) | KD (nM) |
|---|---|---|---|---|---|---|---|
| FabA-dsscFv (CL-dsscFv) | HSA | Titration | 50nM, 25nM, 12.5nM, 6.25nM | 1.83E+05 | 2.40E-04 | 1.31E-09 | 1.31 |
| | | Single concentration | 50nM | 1.65E+05 | 2.11E-04 | 1.28E-09 | 1.28 |
| FabA-dsscFv (CH1-dsscFv) | HSA | Titration | 50nM, 25nM, 12.5nM, 6.25nM | 1.72E+05 | 2.22E-04 | 1.29E-09 | 1.29 |
| | | Single concentration | 50nM | 1.60E+05 | 1.99E-04 | 1.25E-09 | 1.25 |
| FabA-dsFv | HSA | Titration | 50nM, 25nM, 12.5nM, 6.25nM | 7.51E+04 | 1.51E-04 | 2.01E-09 | 2.01 |
| | | Single concentration | 50nM | 6.06E+04 | 1.19E-04 | 1.96E-09 | 1.96 |

|  | Analyte | | Conc. | ka (1/Ms) | kd (1/s) | KD (M) | KD (pM) |
|---|---|---|---|---|---|---|---|
| FabA-dsscFv (CH1-dsscFv) | AntigenA | Single conc. | 25nM | 1.66E+05 | 2.34E-05 | 1.41E-10 | 141 |
| FabA-dsscFv (CL-dsscFv) | AntigenA | Single conc. | 25nM | 1.78E+05 | 1.82E-05 | 1.02E-10 | 102 |
| FabA-dsFv | AntigenA | Single conc. | 25nM | 1.70E+05 | 1.53E-05 | 9.00E-11 | 90 |

FabA-dsscFv (CHO)

1 FabA-dsscFv (CL-dsscFv)
2 FabA-dsscFv (CH1-dsscFv)
3 FabA-dsFv

| Predicted Mr | kDa |
|---|---|
| FabA-dsscFv (CL-dsscFv) | |
| CL-dssFv | 50.5 |
| HC | 23.1 |
| FabA-dsscFv (CH1-dsscFv) | |
| CH1-dsscFv | 50.2 |
| LC | 25.6 |
| FabA-dsFv | |
| CL-vL | 36.3 |
| CH1-vH | 37.3 |

Thermostability FabA-dsscFv (CHO)

| | Tm 1 | Tm 1 std dev | Tm 2 | Tm 2 std dev | Tm 3 | Tm 3 std dev |
|---|---|---|---|---|---|---|
| FabA-dsscFv (CL-dsscFv) | 83.8 | 0.2 | 73.6 | 0.5 | 52.4 | 0.7 |
| FabA-dsscFv (CH1-dsscFv) | 84.6 | 0.3 | 75.5 | 0.5 | 57.8 | 0.6 |
| FabA-dsFv | 84 | 0.2 | 73.9 | 0.3 | ND | ND |

ALBUMIN BINDING ANTIBODIES AND BINDING FRAGMENTS THEREOF

CROSS-REFERENCE TO RELATED APPLICATIONS

The present application is a Divisional of U.S. application Ser. No. 14/356,181, filed May 5, 2014, now U.S. Pat. No. 9,803,004, issued Oct. 31, 2017, which is a national stage application of PCT/EP2012/072335, filed Nov. 9, 2012, which claims priority under 35 U.S.C. § 119(e) to Provisional Application Ser. No. 61/558,559, filed Nov. 11, 2011, each of which are incorporated herein by reference in their entireties.

The present invention relates to new albumin binding antibodies and fragments thereof. Such antibodies may be used for example, for extending the in vivo serum half-life of drugs or proteins conjugated thereto. Methods for the production of such molecules and pharmaceutical compositions comprising them are also provided.

The high specificity and affinity of antibodies makes them ideal diagnostic and therapeutic agents, particularly for modulating protein:protein interactions. Advances in the field of recombinant antibody technology have resulted in the production of antibody fragments, such as Fv, Fab, Fab' and F(ab')$_2$ fragments and other antibody fragments. These smaller molecules retain the antigen binding activity of whole antibodies and can also exhibit improved tissue penetration and pharmacokinetic properties in comparison to whole immunoglobulin molecules. Indeed, antibody fragments are proving to be versatile therapeutic agents, as seen by the recent success of products such as ReoPro® and Lucentis®. Whilst such fragments appear to exhibit a number of advantages over whole immunoglobulins, they also suffer from an increased rate of clearance from serum since they lack the Fc domain that imparts a long lifetime in vivo (Medasan et al., 1997, J. Immunol. 158:2211-2217).

Means to improve the half-life of antibody fragments, such as Fv, Fab, Fab', F(ab')$_2$ and other antibody fragments, are known. One approach has been to conjugate the fragment to polymer molecules. Thus, the short circulating half-life of Fab', F(ab')$_2$ fragments in animals has been improved by conjugation to polyethylene glycol (PEG; see, for example, WO98/25791, WO99/64460 and WO98/37200). Another approach has been to modify the antibody fragment by conjugation to an agent that interacts with the FcRn receptor (see, for example, WO97/34631). Yet another approach to extend half-life has been to use polypeptides that bind serum albumin (see, for example, Smith et al., 2001, Bioconjugate Chem. 12:750-756; EP0486525; U.S. Pat. No. 6,267,964; WO04/001064; WO02/076489; and WO01/45746). Serum albumin is an abundant protein in both vascular and extravascular compartments with a half-life in man of about 19 days (Peters, 1985, Adv Protein Chem. 37:161-245). This is similar to the half-life of IgG1, which is about 21 days (Waldeman & Strober, 1969, Progr. Allergy, 13:1-110).

Anti-serum albumin binding single variable domains have been described along with their use as conjugates to increase the half-life of drugs, including NCE (chemical entity) drugs, proteins and peptides, see for example, Holt et al., Protein Engineering, Design & Selection, vol 21, 5, pp 283-288, WO04003019, WO2008/096158, WO05118642, WO2006/0591056 and WO2011/006915. Other anti-serum albumin antibodies and their use in multispecific antibody formats have been described in WO2009/040562, WO2010/035012 and WO2011/086091. In particular two variable domains known as 645gH1 and 645gL1 having the sequences given herein in SEQ ID NO:9 and SEQ ID NO:10 have already been described.

The present invention provides improved albumin binding antibodies derived from those sequences. Advantageously, the antibodies of the present disclosure have affinity comparable to the starting antibody and in addition may have one or more properties which render them suitable for use in a therapeutic product, for example reduced immunogenicity, increased stability, improved expression or similar.

Preferably the antibodies of the invention bind human serum albumin.

In one embodiment the antibodies of the present invention bind cynomolgus serum albumin, murine serum albumin and/or rat serum albumin.

In one embodiment the present invention provides an albumin binding antibody or fragment thereof comprising a heavy chain variable region having the sequence given in SEQ ID NO:1 or SEQ ID NO:2.

In one embodiment the present invention provides albumin binding antibody or fragment thereof comprising a light chain variable region having the sequence given in SEQ ID NO:3 or SEQ ID NO:4.

In one embodiment the present invention provides an albumin binding antibody or fragment thereof comprising a heavy chain variable region having the sequence given in SEQ ID NO:1 or SEQ ID NO:2 and a light chain variable region having the sequence given in SEQ ID NO:3 or SEQ ID NO:4.

In one embodiment the heavy chain variable region has a cysteine at position 44 of the heavy chain and has the sequence given in SEQ ID NO:2.

In one embodiment the light chain variable region has a cysteine at position 100 of the light chain and has the sequence given in SEQ ID NO:4.

The antibody variable regions of the present invention may be incorporated into any suitable antibody format. Such antibodies include whole antibodies and functionally active fragments or derivatives thereof. Accordingly, such albumin binding antibodies may comprise a complete antibody molecule having full length heavy and light chains or a fragment thereof and may be, but are not limited to Fab, modified Fab, Fab', F(ab')$_2$, Fv, single variable domain antibodies, scFv, bi, tri or tetra-valent antibodies, Bis-scFv, diabodies, triabodies, tetrabodies, tribodies, DVD-Ig, DART, BiTE and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Multi-valent antibodies may comprise multiple specificities or may be monospecific (see for example WO 92/22853, WO 99/37791 and WO05/113605). Other multivalent/multispecific formats include those described in WO2009/040562, WO2010/035012 and WO2011/086091 including the Fab-Fv and Fab-dsFv illustrated herein in FIGS. 1A and 1B respectively.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when antibody effector functions are required. Alternatively, IgG2 and IgG4 isotypes may be used when antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995).

In one embodiment the antibody heavy chain comprises a CH1 domain and the antibody light chain comprises a CL domain, either kappa or lambda.

It will be appreciated that such albumin binding antibodies or fragments thereof, may be conjugated to any other antibodies or fragments thereof, other proteins such as enzymes, hormones, cytokines, peptides or other molecules or drugs, as desired. The albumin binding antibodies of the present invention are particularly useful in extending the serum half-life of such entities conjugated thereto.

In one example the albumin binding antibody of the present invention is linked, covalently or non-covalently, to a selected therapeutic or diagnostic compound. Suitable therapeutic compounds may include, for example, receptor agonists or antagonists, enzyme inhibitors, metal chelators, anti-viral agents, anti-fungal agents, cardiovascular drugs and chemotherapeutic drugs.

In one embodiment an albumin binding antibody or fragment thereof according to the present invention is fused or conjugated to a second antibody or fragment thereof which binds to an antigen of interest.

In one embodiment, an antigen of interest bound by the second antibody or antibody fragment may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD134 (OX40), ICOS, BCMP7, CD137, CD27L, CDCP1, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, and VEGF, and where appropriate, receptors thereof.

Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody or fragment thereof may be used to functionally alter the activity of the antigen of interest. For example, the antibody may neutralize, antagonize or agonise the activity of said antigen, directly or indirectly.

The antibody or fragment thereof conjugated to the albumin binding antibody of the present invention can be from any species but are preferably derived from a monoclonal antibody, a fully human antibody or a humanised antibody. An antibody fragment for use in the present invention can be derived from any class (e.g. IgG, IgE, IgM, IgD or IgA) or subclass of immunoglobulin molecule and may be obtained from any species including for example mouse, rat, shark, rabbit, pig, hamster, camel, llama, goat or human.

In one embodiment, the antibody is a Fab or Fab' fragment which is a monoclonal, fully human, humanized or chimeric antibody fragment. In one embodiment the antibody Fab or Fab' fragments are fully human or humanised.

Monoclonal antibodies may be prepared by any method known in the art such as the hybridoma technique (Kohler & Milstein, *Nature,* 1975, 256, 495-497), the trioma technique, the human B-cell hybridoma technique (Kozbor et al., *Immunology Today,* 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA,* 1996, 93(15), 7843-7848, WO 92/02551, WO2004/051268 and WO2004/106377.

Humanized antibodies are antibody molecules from non-human species having one or more complementarity determining regions (CDRs) from the non-human species and a framework region from a human immunoglobulin molecule (see, for example, U.S. Pat. No. 5,585,089).

The antibodies for use in the present invention can also be generated using various phage display methods known in the art and include those disclosed by Brinkman et al., *J. Immunol. Methods,* 1995, 182, 41-50; Ames et al., *J. Immunol. Methods,* 1995, 184, 177-186; Kettleborough et al. *Eur. J. Immunol.,* 1994, 24, 952-958; Persic et al., *Gene,* 1997 187, 9-18; and Burton et al., *Advances in Immunology,* 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108. Also, transgenic mice, or other organisms, including other mammals, may be used to generate humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and/or constant region genes have been replaced by their human counterparts eg. as described in general terms in EP0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 B1 and EP0463151 B1.

The antibody fragment e.g. Fab or Fab' starting material for use in the present invention may be obtained from any whole antibody, especially a whole monoclonal antibody, using any suitable enzymatic cleavage and/or digestion techniques, for example by treatment with pepsin. Alternatively, or in addition the antibody starting material may be prepared by the use of recombinant DNA techniques involving the manipulation and re-expression of DNA encoding antibody variable and/or constant regions. Standard molecular biology techniques may be used to modify, add or delete amino acids or domains as desired. Any alterations to the variable or constant regions are still encompassed by the terms 'variable' and 'constant' regions as used herein.

The antibody fragment starting material may be obtained from any species including for example mouse, rat, rabbit, hamster, camel, llama, goat or human. Parts of the antibody fragment may be obtained from more than one species, for example the antibody fragments may be chimeric. In one example, the constant regions are from one species and the variable regions from another. The antibody fragment starting material may also be modified. In another example, the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibody fragments are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In one example an albumin binding variable domain of the present invention is fused to a single domain antibody or dAb. Single variable domains also known as single domain antibodies or dAbs for use in the present invention can be generated using methods known in the art and include those disclosed in WO2005118642, Ward et al., 1989, Nature, 341, 544-546 and Holt et al., 2003, Trends in Biotechnology, 21, 484-490. In one embodiment a single domain antibody for use in present invention is a heavy chain variable domain (VH) or a light chain domain (VL). Each light chain domain may be either of the kappa or lambda subgroup. Methods for isolating VH and VL domains have been described in the art, see for example EP0368684 and Ward et al., supra. Such domains may be derived from any suitable species or antibody starting material. In one embodiment the single domain antibody may be derived from a rodent, a human or other species. In one embodiment the single domain antibody is humanised.

In one embodiment the single domain antibody is derived from a phage display library, using the methods described in for example, WO2005/118642, Jespers et al., 2004, Nature Biotechnology, 22, 1161-1165 and Holt et al., 2003, Trends in Biotechnology, 21, 484-490. Preferably such single domain antibodies are fully human but may also be derived from other species. In one embodiment the single variable domain is chimeric in that the framework is human or substantially human in origin and the CDR(s) is/are of non-human origin. It will be appreciated that the sequence of the single domain antibody once isolated may be modified to improve the characteristics of the single domain antibody, for example solubility, as described in Holt et al., supra.

Substantially human as employed herein is intended to refer that the human character of the original material is retained, which may be relevant to immunogenicity. Substantially human material would include wherein one amino acid in the framework sequence is added deleted or replaced by another amino acid.

In one embodiment the dAb is a human sequence obtained from scFv phage-display or from a transgenic Humouse™ or Velocimouse™ or a humanised rodent.

In one embodiment, the dAb is obtained from a human or humanised rodent, a camelid or a shark. Such a dAb will preferably be humanised. In one example the single domain antibody is a VHH domain based on camelid immunoglobulins as described in EP0656946. In one example, a camel or a llama is immunised with an antigen of interest and blood collected when the titre is appropriate. The gene encoding the dAb may be cloned by single cell PCR, or the B cell(s) encoding the dAb may be immortalised by EBV transformation, or by fusion to an immortal cell line.

In one example, one or more of the antibody variable domains of the present invention are incorporated into a multivalent antibody format as described in WO2009/040562, WO2010/035012 or WO2011/086091. Such formats can be monospecific, bispecific or trispecific. Thus, in one preferred embodiment, the antibody fusion proteins of the invention are translation fusion proteins, i.e. genetic fusions, the sequence of each of which is encoded by an expression vector. Alternatively, the antibody fusion protein components may be fused using chemical means, i.e. by chemical conjugation or chemical cross-linking. Such chemical means are known in the art.

Figure 1B:
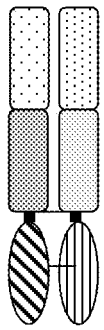

Examples of such translation fusion proteins, with and without disulphide bonds are illustrated in FIGS. 1A and 1B.

Accordingly, in one embodiment there is provided a multi-specific antibody fusion protein comprising an antibody Fab or Fab' fragment with specificity for an antigen of interest, said fragment being fused to at least one single variable domain sequence which has specificity for human serum albumin having the SEQ given in SEQ ID NO:1, 2, 3 or 4.

In one example, the albumin binding antibody variable domains of the present invention are fused to antibody fragments, such as Fab' fragments which possess a native or a modified hinge region. Where the antibody fragment for use in preparing such a fusion protein of the invention is a Fab' fragment, said fragment is generally extended at the C-terminus of the heavy chain by one or more amino acids. Thus, an antibody fusion of the invention can comprise a Fab' fragment translation fused (or chemically fused) to an albumin binding variable region, directly or via a linker. Further, examples of suitable antibody Fab' fragments include those described in WO2005003170 and WO2005003171.

In another example, the antibody fragments are Fab fragments. Thus, an antibody fusion of the invention can comprise a Fab fragment translation fused (or chemically fused) to a linker sequence which in turn is translation fused (or chemically fused) to one or more albumin binding variable regions. Preferably, the Fab fragment is a Fab fragment which terminates at the interchain cysteines, as described in WO2005/003169.

In the present invention each anti-albumin variable domain fused to a Fab or Fab' fragment may linked directly or via a linker.

Linked directly as employed herein is intended to refer to the fact that the "last" amino acid of the Fab or Fab' is joined by a peptide bond to the "first" amino acid of the single variable domain of an albumin binding antibody of the present invention (or indeed vice versa).

Examples of suitable linker regions for linking a variable domain to a Fab or Fab' include, but are not limited to, flexible linker sequences and rigid linker sequences. Flexible linker sequences include those disclosed in Huston et al., 1988, PNAS 85:5879-5883; Wright & Deonarain, Mol. Immunol., 2007, 44(11):2860-2869; Alfthan et al., Prot. Eng., 1995, 8(7):725-731; Luo et al., J. Biochem., 1995, 118(4):825-831; Tang et al., 1996, J. Biol. Chem. 271(26): 15682-15686; and Turner et al., 1997, JIMM 205, 42-54 (see Table 1 for representative examples).

TABLE 1

| Flexible linker sequences | |
|---|---|
| SEQ ID NO: | SEQUENCE |
| 21 | SGGGGSE |
| 22 | DKTHTS |
| 23 | (S)GGGGS |
| 24 | (S)GGGGSGGGGS |
| 25 | (S)GGGGSGGGGSGGGGS |
| 26 | (S)GGGGSGGGGSGGGGSGGGGS |
| 27 | (S)GGGGSGGGGSGGGGSGGGGSGGGGS |
| 28 | AAAGSG-GASAS |
| 29 | AAAGSG-XGGGS-GASAS |
| 30 | AAAGSG-XGGGSXGGGS-GASAS |
| 31 | AAAGSG-XGGGSXGGGSXGGGS-GASAS |
| 32 | AAAGSG-XGGGSXGGGSXGGGSXGGGS-GASAS |
| 33 | AAAGSG-XS-GASAS |
| 34 | PGGNRGTTTTRRPATTTGSSPGPTQSHY |
| 35 | ATTTGSSPGPT |
| 36 | ATTTGS |
| — | GS |
| 37 | EPSGPISTINSPPSKESHKSP |
| 38 | GTVAAPSVFIFPPSD |
| 39 | GGGGIAPSMVGGGGS |
| 40 | GGGGKVEGAGGGGS |

TABLE 1-continued

| Flexible linker sequences | |
|---|---|
| SEQ ID NO: | SEQUENCE |
| 41 | GGGGSMKSHDGGGGS |
| 42 | GGGGNLITIVGGGGS |
| 43 | GGGGVVPSLPGGGGS |
| 44 | GGEKSIPGGGGS |
| 45 | RPLSYRPPFPFGFPSVRP |
| 46 | YPRSIYIRRRHPSPSLTT |
| 47 | TPSHLSHILPSFGLPTFN |
| 48 | RPVSPFTFPRLSNSWLPA |
| 49 | SPAAHFPRSIPRPGPIRT |
| 50 | APGPSAPSHRSLPSRAFG |
| 51 | PRNSIHFLHPLLVAPLGA |
| 52 | MPSLSGVLQVRYLSPPDL |
| 53 | SPQYPSPLTLTLPPHPSL |
| 54 | NPSLNPPSYLHRAPSRIS |
| 55 | LPWRTSLLPSLPLRRRP |
| 56 | PPLFAKGPVGLLSRSFPP |
| 57 | VPPAPVVSLRSAHARPPY |
| 58 | LRPTPPRVRSYTCCPTP- |
| 59 | PNVAHVLPLLTVPWDNLR |
| 60 | CNPLLPLCARSPAVRTFP |

(S) is optional in sequences 23 to 27.
Examples of rigid linkers include the peptide sequences GAPAPAAPAPA (SEQ ID NO: 61), PPPP (SEQ ID NO: 62) and PPP.

In one embodiment, an antibody hinge sequence or part thereof is used as a linker, eg. the upper hinge sequence. Typically, antibody Fab' fragments for use in the present invention possess a native or a modified hinge region. Such hinge regions are used as a natural linker to the albumin binding variable domain moiety. The native hinge region is the hinge region normally associated with the $C_H1$ domain of the antibody molecule. A modified hinge region is any hinge that differs in length and/or composition from the native hinge region. Such hinges can include hinge regions from any other species, such as human, mouse, rat, rabbit, hamster, camel, llama or goat hinge regions. Other modified hinge regions may comprise a complete hinge region derived from an antibody of a different class or subclass from that of the $C_H1$ domain. Thus, for instance, a $C_H1$ domain of class γ1 may be attached to a hinge region of class γ4. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as alanine, or by converting suitably placed residues into cysteine residues. By such means the number of cysteine residues in the hinge region may be increased or decreased. In addition other characteristics of the hinge can be controlled, such as the distance of the hinge cysteine(s) from the light chain interchain cysteine, the distance between the cysteines of the hinge and the composition of other amino acids in the hinge that may affect properties of the hinge such as flexibility e.g. glycines may be incorporated into the hinge to increase rotational flexibility or prolines may be incorporated to reduce flexibility. Alternatively combinations of charged or hydrophobic residues may be incorporated into the hinge to confer multimerisation properties, see for example, Richter et al., 2001, Prot. Eng. 14(10):775-783 for use of charged or ionic tails, e.g., acidic tails as linkers and Kostelny et al., 1992, J. Immunol. 5(1):1547-1553 for leucine zipper sequences. Other modified hinge regions may be entirely synthetic and may be designed to possess desired properties such as length, composition and flexibility.

A number of modified hinge regions have already been described for example, in U.S. Pat. No. 5,677,425, U.S. Pat. No. 6,642,356, WO9915549, WO2005003170, WO2005003169, WO2005003170, WO9825971 and WO2005003171 and these are incorporated herein by reference. Such hinges generally follow on from the CH1 region, but may also be incorporated onto the end of constant region of a light chain kappa or lambda fragment; see Table 3 for examples.

TABLE 3

Hinge linker sequences

| SEQ ID NO: | SEQUENCE |
|---|---|
| 63 | DKTHTCAA |
| 64 | DKTHTCPPCPA |
| 65 | DKTHTCPPCPATCPPCPA |
| 66 | DKTHTCPPCPATCPPCPATCPPCPA |
| 67 | DKTHTCPPCPAGKPTLYNSLVMSDTAGTCY |
| 68 | DKTHTCPPCPAGKPTHVNVSVVMAEVDGTCY |
| 69 | DKTHTCCVECPPCPA |
| 70 | DKTHTCPRCPEPKSCDTPPPCPRCPA |
| 71 | DKTHTCPSCPA |

The antibody variable domains of the present invention are a complementary VH/VL pair which bind the antigen co-operatively i.e. they are a complementary VH/VL pair which have the same binding specificity. They are in fact a VH/VL pair derived from the same antibody.

In one embodiment, the VH domain is fused to the C-terminus of the heavy chain constant region (CH1) and the VL domain is fused to the C-terminus of the light chain constant region (C kappa or C lambda).

In one embodiment the VH and VL are linked by a disulfide bond which is thought to provide additional stabilisation to the construct, which may be advantageous.

In one or more embodiments the disulfide bond between the heavy and light chain constant regions e.g. in a Fab, such as between the CH domain and CL or CK domain is not present, for example because one or more cysteines which form the bond are replaced. Said one or more cysteines may be replaced with, for example serine.

In one or more embodiments an interchain disulfide bond between the heavy and light chain between the CH domain and CL or CK domain is present.

In one example the present invention provides a bispecific antibody fusion protein comprising:

a heavy chain comprising, in sequence from the N-terminal, a first heavy chain variable domain ($V_H1$), a CH1 domain and a second heavy chain variable domain ($V_H2$), a light chain comprising, in sequence from the N-terminal, a first light chain variable domain ($V_L1$), a CL domain and a second light chain variable domain ($V_L2$), wherein said heavy and light chains are aligned such that VH1 and VL1 form a first antigen binding site and VH2 and VL2 form a second antigen binding site, wherein the antigen bound by the second antigen binding site is human serum albumin and wherein the second heavy chain variable domain ($V_H2$) has the sequence given in SEQ ID NO:1 and the second light chain variable domain ($V_L2$) has the sequence given in SEQ ID NO: 3.

In one embodiment the albumin binding heavy and light chain variable regions are linked by a disulphide bond. Accordingly, in one example, the present invention provides a bispecific antibody fusion protein comprising:

a heavy chain comprising, in sequence from the N-terminal, a first heavy chain variable domain ($V_H1$), a CH1 domain and a second heavy chain variable domain ($V_H2$), a light chain comprising, in sequence from the N-terminal, a first light chain variable domain ($V_L1$), a CL domain and a second light chain variable domain ($V_L2$), wherein said heavy and light chains are aligned such that VH1 and VL1 form a first antigen binding site and VH2 and VL2 form a second antigen binding site, wherein the antigen bound by the second antigen binding site is human serum albumin, wherein the second heavy chain variable domain ($V_H2$) has the sequence given in SEQ ID NO:2 and the second light chain variable domain ($V_L2$) has the sequence given in SEQ ID NO: 4 and the second heavy chain variable domain ($V_H2$) and second light chain variable domain ($V_L2$) are linked by a disulphide bond.

In one example, the present invention provides a multispecific antibody fusion protein comprising:

a heavy chain comprising, in sequence from the N-terminal, a first heavy chain variable domain ($V_H1$), a CH1 domain, a second heavy chain variable domain ($V_H2$) and a third heavy chain variable domain ($V_H3$), a light chain comprising, in sequence from the N-terminal, a first light chain variable domain ($V_L1$), a CL domain, a second light chain variable domain ($V_L2$) and a third light chain variable domain ($V_L3$), wherein said heavy and light chains are aligned such that VH1 and VL1 form a first antigen binding site and VH2 and VL2 form a second antigen binding site and VH3 and VL3 form a third antigen binding site, wherein the antigen bound by the second or third antigen binding site is human serum albumin and wherein the second or third heavy chain variable domain has the sequence given in SEQ ID NO:1 or SEQ ID NO:2 and the second or third light chain variable domain has the sequence given in SEQ ID NO: 3 or SEQ ID NO: 4.

It will be appreciated that there may be linkers between one or more of the domains listed above. In particular there may be a linker between CL and VL2 and CH1 and VH2 and where present, a linker between VL2 and VL3 and VH2 and VH3. Suitable linkers have already been described herein above. Additional linkers are provided in FIGS. 2 (e) and (f), SEQ ID NOs 5 and 6.

In one embodiment the antibody is a scFv. In one embodiment the antibody is a scFv where the variable domains (VH and VL) are linked by the linker given in SEQ ID NO:17.

The antibody variable domains of the present invention bind to albumin with a binding affinity sufficient to extend the half-life of the conjugate, such as a Fab or Fab' in vivo. It has been reported that an affinity for albumin of less than or equal to 2.5 µM affinity will extend half-life in vivo (Nguyen, A. et al (2006) Protein Engineering, Design & Selection, 19(7), 291-297). In one example the variable domain antibody pair of the present invention has a high binding affinity, for example 3 nM nanomolar. In one example the single domain antibodies have a binding affinity for antigen which is nanomolar or micromolar. Affinity may be measured using any suitable method known in the art, including surface Plasmon resonance using natural or recombinant serum albumin.

Preferably the albumin binding antibody of the present invention has a binding affinity for human serum albumin of about 1 µM or better. In one embodiment the antibody has a binding affinity of about 500M or less. In one embodiment the antibody has a binding affinity of about 200 nM or less. In one embodiment the antibody has a binding affinity of about 100 nM or less. In one embodiment the antibody has a binding affinity of about 50 nM or less. In one embodiment the antibody has a binding affinity of about 20 nM or less. In one embodiment the antibody has a binding affinity of about 10 nM or less. In one embodiment the antibody has a binding affinity of about 5 nM or less. In one embodiment the antibody has a binding affinity of about 2 nM or less. In one embodiment the antibody has a binding affinity of about 1 nM or less. It will be appreciated that the affinity of antibodies provided by the present invention may be altered using any suitable method known in the art. The present invention therefore also relates to variants of the antibody molecules of the present invention, which have an improved affinity for albumin. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The present invention also provides an isolated DNA sequence encoding an albumin binding antibody or fusion protein of the present invention. The DNA sequences of the present invention may comprise synthetic DNA, for instance produced by chemical processing, cDNA, genomic DNA or any combination thereof.

DNA sequences which encode the dual specificity antibody fusion proteins of the present invention can be obtained by methods well known to those skilled in the art. For example, DNA sequences coding for part or all of the antibody fragments, linkers and/or dAbs may be synthesised as desired from the determined DNA sequences or on the basis of the corresponding amino acid sequences.

Standard techniques of molecular biology may be used to prepare DNA sequences coding for the dual specificity antibody fusion protein of the present invention. Desired DNA sequences may be synthesised completely or in part using oligonucleotide synthesis techniques. Site-directed mutagenesis and polymerase chain reaction (PCR) techniques may be used as appropriate.

The present invention further relates to a cloning or expression vector comprising one or more DNA sequences of the present invention. Accordingly, provided is a cloning or expression vector comprising one or more DNA sequences encoding a dual specificity antibody fusion protein of the present invention. In one preferred embodiment, the cloning or expression vector comprises a single DNA sequence encoding the entire dual specificity antibody fusion protein. Thus, the cloning or expression vector comprises DNA encoded transcription units in sequence such that a translation fusion protein is produced.

Indeed, it will be understood by those skilled in the art that a fusion protein of the invention can have the albumin binding variable domain at the N-terminus or the C-terminus and thus, the albumin binding DNA encoded transcription unit will be first or last, respectively, within the DNA sequence encoding the translation fusion. Thus, a translation fusion may comprise an N-terminal variable domain and a C-terminal Fab or Fab'. Further, a translation fusion may comprise an N-terminal Fab or Fab' and a C-terminal albumin binding variable domain.

It will be appreciated that the heavy chain and light chain of antibody or fragment thereof may be incorporated into the same or different vectors. In one embodiment one vector may comprise a translation fusion comprising a heavy chain and another vector may comprise a translation fusion comprising a light chain.

DNA code for an antibody fragment comprised within a translation fusion of the invention can be incorporated into a vector as a transcription unit in configurations as known to the person skilled in the art, for example a transcription unit can comprise code for the light chain followed by the heavy chain code, or vice versa; see, in particular, Humphreys et al., 2002, Protein Expression and Purification, 26:309-320.

Preferably, a vector according to the present invention comprises an appropriate leader sequence, such as an antibody leader sequence. Such leader sequences are well known in the art.

General methods by which the vectors may be constructed, transfection and transformation methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding a dual specificity antibody fusion protein of the present invention. Any suitable host cell/vector system may be used for expression of the DNA sequences encoding the dual specificity antibody fusion protein. Bacterial, for example *E. coli*, and other microbial systems may be used or eukaryotic, for example mammalian, host cell expression systems may also be used. Suitable mammalian host cells include NS0, CHO, myeloma or hybridoma cells. Accordingly in one embodiment the fusion protein of the present invention is expressed in *E. coli*. In another embodiment the fusion protein of the present invention is expressed in mammalian cells.

The present invention also provides a process for the production of an albumin binding antibody or fusion protein comprising culturing a host cell comprising a vector of the present invention under conditions suitable for the expression of protein from the DNA sequence encoding said albumin binding antibody. The invention further provides methods for isolating the albumin binding antibody.

On production, an albumin binding antibody of the present invention may be purified, where necessary, using any suitable method known in the art. For example, but without limitation, chromatographic techniques such as ion exchange, size exclusion, protein G or hydrophobic interaction chromatography may be used.

The size of the antibody or antibody fusion protein may be confirmed by conventional methods known in the art such as size exclusion chromatography and non-reducing SDS-PAGE. Such techniques can be used, for example to confirm that the protein has not dimerised and/or does not have a portion missing. If dimers are detected and a homogenous monomeric product is required then the monomeric antibody fusion protein may be purified away from the dimeric species using conventional chromatography techniques as described above. In the present invention the improved variable regions provided in SEQ ID NOs 1 to 4 result in more monomer being produced.

Antibodies, conjugates and fusion proteins of the invention are useful in the treatment of diseases or disorders including inflammatory diseases and disorders, immune disease and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, lung, kidney, pancreas, stomach, bladder or bowel. Cancers tend to infiltrate into adjacent tissue and spread (metastasise) to distant organs, for example: to bone, liver, lung or the brain.

Thus, according to a further aspect of the invention, there is provided a pharmaceutical composition which comprises an antibody, antibody fusion or conjugate of the invention in association with one or more pharmaceutically acceptable carriers, excipients or diluents. Also provided is the use of an antibody fusion protein of the invention for the manufacture of a medicament for the treatment of a disease or disorder. Most preferably, the disease or disorder is an inflammatory disease or disorder.

Pharmaceutical compositions according to the invention may take a form suitable for oral, buccal, parenteral, subcutaneous, nasal, topical, ophthalmic or rectal administration, or a form suitable for administration by inhalation or insufflation.

Where appropriate, for example if the single domain antibody or antibodies of the antibody fusion protein bind to albumin, it may be desirable to pre-formulate the dual specificity fusion protein with human or recombinant serum albumin, using any suitable method known in the art.

Where the pharmaceutical formulation is a liquid, for example a solution or suspension then the formulation may further comprise albumin, for example human serum albumin, in particular recombinant albumin such as recombinant human serum albumin. Suitable amounts may be in the range of less than 2% w/w of the total formulation, in particular less than 1, 0.5, or 0.1% w/w. This may assist in stabilizing the antibody component in the formulation. The pharmaceutical composition may be lyophilized for reconstitution later, with an aqueous solvent.

In one embodiment there is provided a unit dose container, such as a vial, comprising a lyophilized "antibody" according to the invention.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The antibodies, fusion and/or conjugates of the invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the antibodies of the invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody formats of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The antibodies formats of the present disclosure are thought to be suitable for delivery via nebulisation.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The invention will now be described with reference to the following examples, which are merely illustrative and should not in any way be construed as limiting the scope of the present invention.

LIST OF FIGURES

Figure 6:
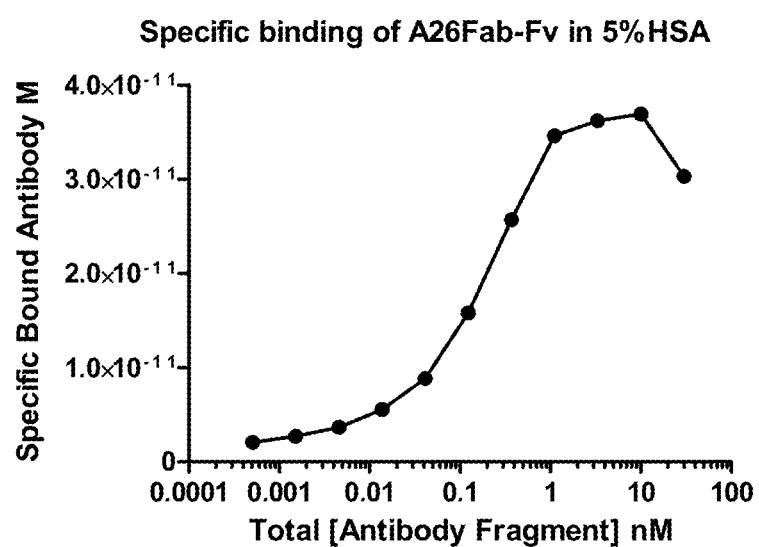
Figure 7:
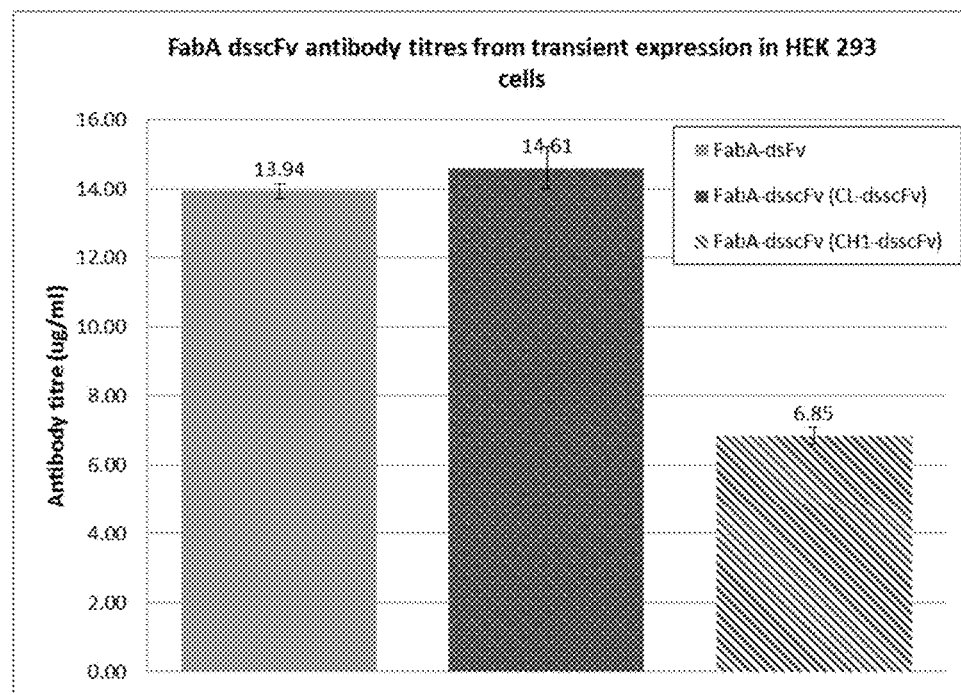
Figure 8:
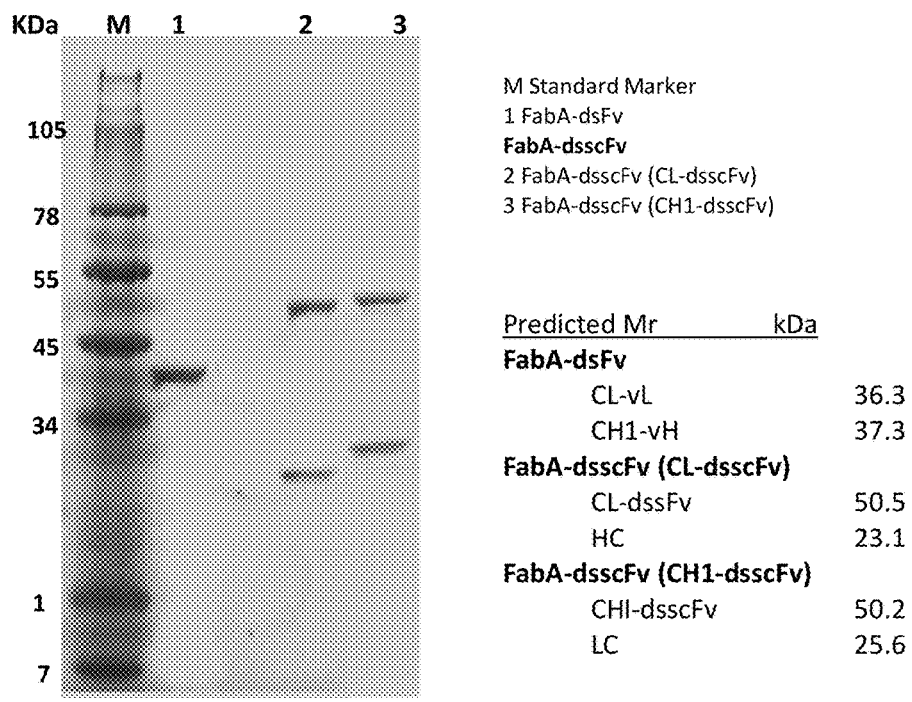
Figures 10, 11:
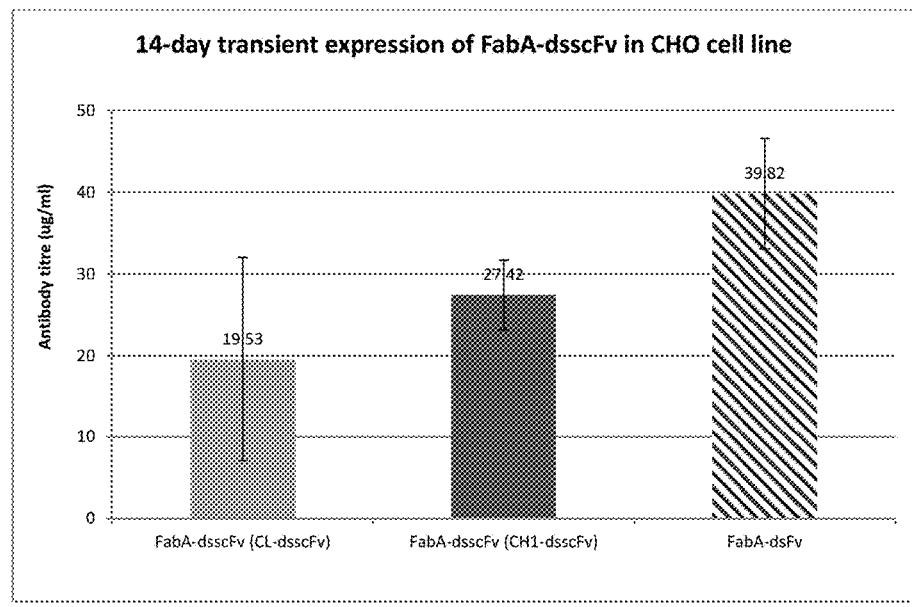
Figures 12, 13:
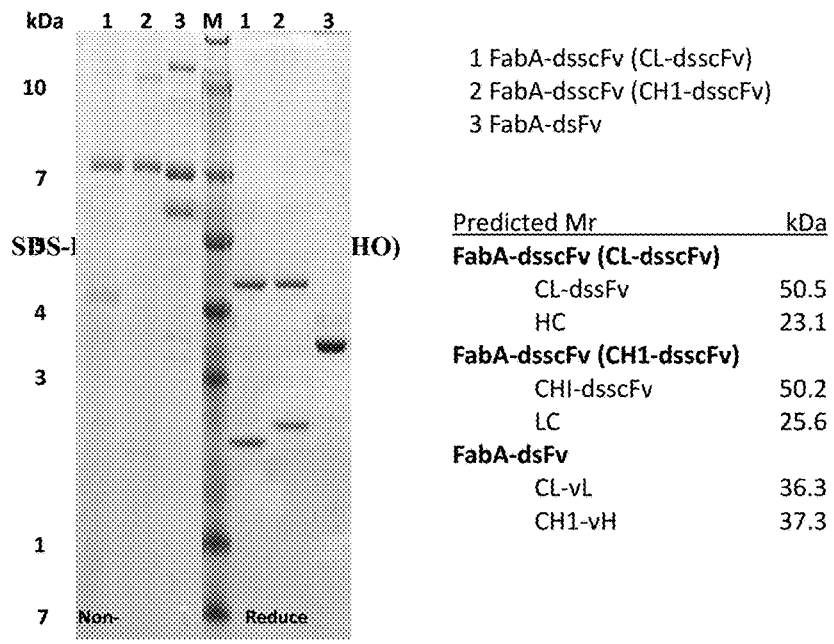

FIG. 1A: Diagrammatic representation of a Fab-Fv
FIG. 1B: Diagrammatic representation of a Fab-dsFv
FIGS. 2 to 5: Sequences of the present invention
FIG. 6: Shows binding of AlexaFluor 488 labelled A26 Fab-dsFv to activated human $CD4^+OX40^+$ T cells
FIG. 7: Shows ug/ml of antibody constructs produced by transient expression in HEK293 cells
FIG. 8 Shows SDS-PAGE of Fab disulphide stabilised scFv.
FIG. 9 Shows tabulated data relating to the binding affinity to human serum albumin of various constructs
FIG. 10 Shows tabulated data of affinity Fab binding antigen of various constructs
FIG. 11 Shows ug/ml of antibody constructs produced by transient expression in CHO cells
FIG. 12 Shows SDS-PAGE analysis of various constructs
FIG. 13 Shows thermostablity data for various constructs expressed in CHO cells.

DNA MANIPULATIONS AND GENERAL METHODS

Competent *E. coli* strains were used for transformations and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program Sequencher (Genecodes). Oligonucleotides were obtained from Sigma or Invitrogen. Genes encoding initial V-region sequences were constructed by an automated synthesis approach by DNA2.0, and modified to generate the grafted versions by oligonucleotide directed mutagenesis. The concentration of Fab-Fv was determined by a Protein-G based HPLC method.

EXAMPLE 1

Generation and Analysis of Different Humanisation Grafts of 645 in A26Fab-645dsFv We have previously described the Fab-dsFv antibody format (FIG. 1B) and a humanised anti-albumin antibody known as '645gH1gL1' in WO2010/035012. We have also previously described the generation of a humanised antagonistic anti-OX40 antibody known as 'A26' in WO2010096418. Here we describe the generation of a new improved humanised graft of antibody '645' known as 645dsgH5gL4 and the generation of a Fab-dsFv antibody molecule incorporating that graft in the Fv component and the 'A26' variable regions in the Fab component.

The sequences of 645gH1 and gL1 are given in FIGS. 3(a) and (b), SEQ ID NOs 9 and 10.

Construction of A26Fab-645dsFv(gH1gL1) and A26Fab-645dsFv(gH5gL4) Plasmids

The total coding region of A26Fab-645dsFv(gL1) light chain (SEQ ID NO:12) was cloned into a UCB mammalian expression vector under the control of the HCMV-MIE promoter and SV40E polyA sequence. The light chain variable region of 645dsFv(gL1) (SEQ ID NO:10) was mutated to 645dsFv(gL4) (SEQ ID NO:4) by an overlapping PCR method. The total coding region of A26Fab-645dsFv (gH1) heavy chain (SEQ ID NO:11) was cloned into a UCB mammalian expression vector under the control of the HCMV-MIE promoter and SV40E polyA sequence. The heavy chain variable region of 645dsFv(gH1) (SEQ ID NO:9) was mutated to 645dsFv(gH5) (SEQ ID NO:2) by an overlapping PCR method. The constructs were verified by sequencing.

Mammalian Expression of A26Fab-645dsFv(gH1gL1) and A26Fab-645dsFv(gH5gL4)

HEK293 cells were transfected with the heavy and light chain plasmids using Invitrogen's 293fectin transfection reagent according to the manufacturer's instructions. Briefly, 25 µg heavy chain plasmid and 25 µg light chain plasmid were incubated with 100 µl 293fectin and 1700 µl Optipro media for 20 mins at RT. The mixture was then added to $50 \times 10^6$ HEK293 cells in 50 ml suspension and incubated for 6 days with shaking at 37° C. After 6 days the supernatant was collected by centrifugation at 1500×g for 10 minutes to remove the cells and then 0.22 µm sterile filtered.

Protein-G Purification of A26Fab-645dsFv(gH1gL1) and A26Fab-645dsFv(gH5gL4)

The ~50 ml of 0.22 µm filtered supernatants were concentrated to ~2 ml using Amicon Ultra-15 concentrators with a 10 kDa molecular weight cut off membrane and centrifugation at 4000×g in a swing out rotor. 1.8 ml of concentrated supernatant was applied at 1 ml/min to a 1 ml Gammabind Plus Sepharose (GE Healthcare) column equilibrated in 20 mM phosphate, 40 mM NaCl pH7.4. The column was washed with 20 mM phosphate, 40 mM NaCl pH7.4 and the bound material eluted with 0.1M glycine/HCl pH2.7. The elution peak was collected and pH adjusted to ~pH7 with 2M Tris/HCl pH8.5. The pH adjusted elution was concentrated and diafiltered into 20 mM phosphate, 150 mM NaCl pH7.4 using Amicon Ultra-15 concentrators with a 10 kDa molecular weight cut off membrane and centrifugation at 4000×g in a swing out rotor, to a final volume of ~0.3 ml.

Size Exclusion Analysis A26Fab-645dsFv(gH1gL1) and A26Fab-645dsFv(gH5gL4)

Protein-G purified samples were analysed by size exclusion HPLC. The samples were separated on a Superdex 200 10/300 GL Tricorn column (GE Healthcare) developed with an isocratic gradient of PBS pH7.4 at 1 ml/min. Peak detection was at 280 nm and apparent molecular weight was calculated by comparison to a standard curve of known molecular weight proteins verses elution volume. Changing the humanisation graft of the 645dsFv from gH1gL1 to gH5gL4 resulted in an increase in the percentage monomer of the expressed A26Fab-645dsFv from 59% to 71% an increase of 12%, without any change in the thermal stability of the dsFv (data not shown) or in the affinity of binding of the dsFv to HSA (data not shown).

EXAMPLE 2

2.1 BIAcore Kinetics for A26 Fab-dsFv (645gH5gL4) Binding OX40

In this and all subsequent examples the A26 Fab-dsFv 645gH5gL4 had the heavy chain sequence given in SEQ ID NO:7 (FIG. 2(g)) and the light chain sequence given in SEQ ID NO:8 (FIG. 2(h)) i.e. the heavy chain contained the G4S, G4T, G4S linker given in SEQ ID NO:5, FIG. 2(e).

BIA (Biamolecular Interaction Analysis) was performed using a BIAcore T200 (GE Healthcare). Affinipure F(ab')$_2$ Fragment goat anti-human IgG, F(ab')$_2$ fragment specific (Jackson ImmunoResearch) was immobilised on a CM5 Sensor Chip via amine coupling chemistry to a capture level of ≈5000 response units (RUs). HBS-EP buffer (10 mM HEPES pH 7.4, 0.15 M NaCl, 3 mM EDTA, 0.05% Surfactant P20, GE Healthcare) was used as the running buffer with a flow rate of 10 µL/min. A 10 µL injection of A26 Fab' at 0.5 µg/mL or A26Fab-dsFv at 1 µg/mL was used for capture by the immobilised anti-human IgG-F(ab')$_2$. Human OX40 was titrated over the captured A26 at various concentrations (25 nM to 1.5625 nM) at a flow rate of 30 µL/min. The surface was regenerated by 2×10 µL injection of 50 mM HCl, followed by a 5 µL injection of 5 mM NaOH at a flowrate of 104/min. Background subtraction binding curves were analysed using the T200evaluation software (version 1.0) following standard procedures. Kinetic parameters were determined from the fitting algorithm.

| Sample  | ka(1/Ms)        | kd(1/s)  | KD(M)    | KD(pM) |
|---------|-----------------|----------|----------|--------|
| Fab'    | 2.18 ± 0.38 E+05 | 1.00 E−05 | 4.68E−11 | 46.8   |
| Fab-Fv  | 2.55 ± 0.35 E+05 | 1.04 E−05 | 4.12E−11 | 41.2   |

Average of 4 determinations 2.2. BIAcore Kinetics for A26 Fab-dsFv (645gH5gL4) Binding Albumin BIA (Biamolecular Interaction Analysis) was performed using a BIAcore T200 (GE Healthcare). Affinipure F(ab')$_2$ Fragment goat anti-human IgG, F(ab')$_2$ fragment specific (Jackson ImmunoResearch) was immobilised on a CM5 Sensor Chip via amine coupling chemistry to a capture level of ≈5000 response units (RUs). HBS-EP buffer (10 mM HEPES pH 7.4, 0.15 M NaCl, 3 mM EDTA, 0.05% Surfactant P20, GE Healthcare) was used as the running buffer with a flow rate of 10 µL/min. A 10 µL injection of Fab-Fv at 0.75 µg/mL was used for capture by the immobilised anti-human IgG-F(ab')$_2$. Human Serum Albumin (HSA), Mouse Serum albumin (MSA) and Cynomolgus Serum Albumin (CSA) was titrated over the captured Fab-Fv at various concentrations (50 nM to 6.25 nM) at a flow rate of 30 µL/min. The surface was regenerated by 2×10 µL injection of 50 mM HCl, followed by a 5 µL injection of 5 mM NaOH at a flowrate of 10 µL/min. Background subtraction binding curves were analysed using the T200evaluation software (version 1.0) following standard procedures. Kinetic parameters were determined from the fitting algorithm.

| Sample | ka(1/Ms)  | kd(1/s)  | KD(M)    | KD(nM) |
|--------|-----------|----------|----------|--------|
| HSA    | 5.84 E+04 | 1.63 E−04 | 2.93E−09 | 2.93   |
| MSA    | 8.86 E+04 | 3.68 E−04 | 4.16E−09 | 4.16   |
| CSA    | 7.1 E+04  | 1.89 E−04 | 2.66E−09 | 2.66   |

Average of 3 determinations 2.3 Demonstration of A26 Fab-dsFv(645gH5gL4) Binding OX40 and Albumin Simultaneously The simultaneous binding of human OX40 and Human Serum Albumin to A26 Fab-dsFv was assessed. The A26 Fab-dsFv construct was captured to the sensor chip surface as stated in the method for Biacore kinetics for binding A26 Fab-dsFv albumin. 50 nM HAS, 25 nM OX40 or a mixed solution with final concentration of 50 nM HSA and 25 nM OX40 were titrated separately over the captured A26 Fab-dsFv. The binding response for the combined HSA/OX40 solution was equivalent to the sum of the responses of the independent injections. This confirms that the Fab-dsFv is capable of simultaneous binding to both human OX40 and HSA.

| Sample    | Analyte     | Binding (RU) |      |
|-----------|-------------|--------------|------|
| A26 Fab-Fv | hOX40       | 25           |      |
|           | HSA         | 9            |      |
|           | hOX40 + HSA | 35           | (34) |

2.4 Cell-Based Affinity of A26 Fab-dsFv (645gH5gL4)
Methods:
A26 Fab-Fv Binding to Human Activated CD4$^+$OX40$^+$ T Cells.

PBMC were isolated by separation on a Ficoll gradient and activated with 4 µg/mL PHA-L for 3 days at 37° C., 5% CO$_2$, 100% humidity. CD4$^+$ T cells were isolated by negative selection using magnetic beads (CD4$^+$ T cell Isolation Kit II for Human; Miltenyi Biotec). Approximately 1×10$^5$ cells were incubated in the presence of antibody in either Facs buffer (PBS/0.2% BSA/0.09% NaN3) or Facs buffer supplemented with 5% HSA at 4° C. The final concentration of the antibody ranged from 48 nM-0.0005 nM)). The cells were washed in PBS prior to analysis by flow cytometry using a FACScalibur (Becton Dickinson). Two titration data sets were produced in both buffer conditions, one with A26 Fab-dsFv and the second with an irrelevant control Fab-Fv to determine non-specific binding. The number of moles of bound antibody were calculated by using interpolated values from a standard curve generated by use of beads comprised of differing but known amounts of fluorescent dye. Geometric mean fluorescence values were determined in the flow cytometric analyses of cells and beads. Non-specific binding was subtracted from the A26 Fab-dsFv values and the specific binding curve thus generated analysed by non-linear regression using a one-site binding equation (Graphpad Prism®) to determine the K$_D$. To determine the affinity of A26 Fab-dsFv for cell surface expressed antigen, saturation binding experiments were performed using activated CD4$^+$OX40$^+$ T cells, and Alexa Fluor 488-labelled A26 Fab-dsFv. Specific binding of antibody to receptor at equilibrium across a range of antibody concentrations was used to determine K$_D$, assuming that only a very small fraction of antibody was bound to receptor at any point on the binding curve.

Equilibrium binding is described using the following equation:

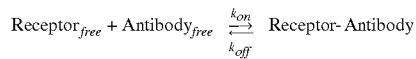

$$\text{Receptor}_{free} + \text{Antibody}_{free} \underset{k_{off}}{\overset{k_{on}}{\rightleftharpoons}} \text{Receptor-Antibody}$$

The rate of association of antibody with receptor=$k_{on}$×[Receptor$_{free}$]×[Antibody$_{free}$]
The rate of dissociation of receptor-antibody complex=$k_{off}$×[Receptor−Antibody]

At equilibrium, the association and dissociation rates are equal and an equation can be derived which describes the binding isotherm; on a semi-log plot the binding is sigmoidal. The $K_D$ is defined by $k_{off}/k_{on}$ and can be calculated from the binding curve as the concentration at which half-maximal binding occurs.

Binding of AlexaFluor488-labelled A26 Fab-Fv to activated human $CD4^{+OX}40^+$ T cells was measured by flow cytometry across a 5-log concentration range.

A representative binding curve for A26 Fab-Fv is shown in FIG. 4.

The mean $K_D$ value obtained on activated cells from 5 different donors is 145 pM.

EXAMPLE 3 EXPRESSION OF $645_2L4_2H5$ AS A SCFV

Plasmid Construction

The scFv were expressed from one of two closely related UCB modified mammalian expression plasmids; pVKΔPvuII was used for cloning and expression of scFv in the HL orientation, whilst pKHΔEcoRV was used for cloning and expression of scFv in the LH orientation. All scFv were designed to contain a 20 amino acid linker peptide, $(GGGGS)_4$ (SEQ ID NO:17) and a C-terminal 10×His tag. The scFv acceptor plasmids 362HL and 240LH encode unique restriction sites at the FW1-FW4 borders of vH (PvuII and XhoI) and vL (EcoRV and BsiWI) enabling the restriction cloning of subsequent scFv variable regions in a two step ligation. Genes encoding 645gH5 vH and 645gL4 vL were synthesised by DNA2.0, with cysteine wobbles at Kabat positions vH44 and vL100 for generation of disulphide-stabilised (ds) scFv. These V-region genes were cloned into acceptor scFv plasmids using PvuII and XhoI (vH) or EcoRV and BsiWI (vL) and successful ligation was verified by DNA sequencing.

Expression and Purification

HEK293F cells (50 ml cultures at $10^6$ cells/ml) were transfected with 50 μg plasmid DNA and cultured at 37° C. in FreeStyle™ media. Supernatants were harvested 6 days post-transfection and scFv were purified by batch $Ni^{2+}$-NTA purification. Purified protein was concentrated and buffer exchanged into PBS for subsequent biophysical characterisation.

Thermostability Assay

Thermofluor assay was performed to assess the thermal stabilities of purified molecules. Purified proteins (0.1 mg/ml) were mixed with SYPRO® Orange dye (Invitrogen), and the mixture dispensed in quadruplicate into a 384 PCR optical well plate. Samples were analysed on a 7900HT Fast Real-Time PCR System (Agilent Technologies) over a temperature range from 20° C. to 99° C., with a ramp rate of 1.1° C./min. Fluorescence intensity changes per well were plotted against temperature and the inflection points of the resulting slopes were used to generate the $T_m$.

Size Exclusion HPLC

Purified proteins (10 μg and 50 μg) were analysed by size exclusion HPLC on a Superdex 200 10/300 GL Tricorn Column (GE Healthcare). An isocratic gradient of PBS pH7.4 was used at a flow rate of 1 ml/min, with UV detection at 214 nm and 280 nm.

Results Summary

645gH5gL4 HLds gave 97% monomer and a Tm in ° C. of 75.6.

645gH5gL4 HL gave 86% monomer and a Tm in ° C. of 75.6.

EXAMPLE 4

Construction of FabA-dsscFv Fusions

Plasmids for Expression in Mammalian Cells.

A single chain Fv (scFv) was constructed by linking the light and heavy chain variable region domains of a human serum albumin binding antibody (SEQ ID: 1 and 3 or 2 and 4) via a flexible linker (SEQ ID: 17) in the HL orientation. Point mutations were introduced into the DNA sequences at selected residues in the framework region of both the heavy chain and the light chain of the Fv. The mutations were introduced to create an interchain disulphide bond between the heavy and light chains of the Fv were heavy chain G44C and light chain G100C to form a disulphide linked-scFv (dsscFv). FabA-dsscFv fusion proteins were constructed by fusing a dsscFv to the C-terminus of the constant region of either the light region (with the Km3 allotype of the kappa constant region), or heavy chain of FabA (human gamma-1 CH1 constant region, γ1 isotype). A flexible (SEQ ID NO: 18 and 5) linker was used to link the scFv to the cKappa region (SEQ ID NO: 19) or CH1 region (SEQ ID NO: 20), respectively. The FabA-dsscFv (CL-dsscFv), FabA-dsscFv (CH1-dsscFv), FabA light chain and FabA heavy chain were manufactured chemically and then cloned into mammalian expression vectors under the control of the HCMV-MIE promoter and SV40E polyA sequence.

Various data for these constructs is shown in FIGS. 7 to 13. Thermostability data for the constructs gave a Tm for each of around 82° C.

Comprising in the context of the present specification is intended to meaning including.

Where technically appropriate embodiments of the invention may be combined. Embodiments are described herein as comprising certain features/elements. The disclosure also extends to separate embodiments consisting or consisting essentially of said features/elements.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

We claim:

1. A method of treating a patient in need thereof comprising the step of administering a therapeutically effective amount of an antibody molecule comprising a serum albumin antibody or antigen-binding fragment thereof comprising a heavy chain variable domain having the sequence given in SEQ ID NO: 1 and a light chain variable domain having the sequence given in SEQ ID NO: 3.

2. A method of treating a patient in need thereof comprising the step of administering a therapeutically effective amount of an antibody molecule comprising a serum albumin antibody or antigen-binding fragment thereof comprising a heavy chain variable domain having the sequence given in SEQ ID NO: 2 and a light chain variable domain having the sequence given SEQ ID NO: 4.

3. A method of treating a patient in need thereof comprising the step of administering a therapeutically effective amount of an antibody molecule comprising a serum albumin antibody fusion protein comprising:

a heavy chain comprising, in sequence from the N-terminal, a first heavy chain variable domain (VH1), a CH1 domain and a second heavy chain variable domain (VH2), a light chain comprising, in sequence from the N-terminal, a first light chain variable domain (VL1), a CL domain and a second light chain variable domain (VL2), wherein said heavy and light chains are aligned such that VH1 and VL1 form a first antigen binding site and VH2 and VL2 form a second antigen binding site, wherein the antigen bound by the second antigen binding site is human serum albumin and wherein the second heavy chain variable domain (VH2) has the sequence given in SEQ ID NO:1 and the second light chain variable domain (VL2) has the sequence given in SEQ ID NO: 3 or the second heavy chain variable domain (VH2) has the sequence given in SEQ ID NO:2 and the second light chain variable domain (VL2) has the sequence given in SEQ ID NO: 4, and the second heavy chain variable domain (VH2) and second light chain variable domain (VL2) are optionally linked by a disulphide bond.

* * * * *

SEQUENCE LISTING

<160> NUMBER OF SEQ ID NOS: 71

<210> SEQ ID NO 1
<211> LENGTH: 121
<212> TYPE: PRT
<213> ORGANISM: Artificial

<220> FEATURE:
<223> OTHER INFORMATION: Heavy chain variable domain of anti-albumin antibody (no ds)

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 2
<211> LENGTH: 121
<212> TYPE: PRT
<213> ORGANISM: Artificial
<220> FEATURE:
<223> OTHER INFORMATION: Heavy chain variable domain of anti-albumin antibody (ds)

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 3
<211> LENGTH: 112
<212> TYPE: PRT
<213> ORGANISM: Artificial
<220> FEATURE:
<223> OTHER INFORMATION: Light chain variable domain of anti-albumin antibody (no ds)

<400> SEQUENCE: 3

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys Arg Thr
            100                 105                 110

<210> SEQ ID NO 4
<211> LENGTH: 112
<212> TYPE: PRT
<213> ORGANISM: Artificial
<220> FEATURE:
<223> OTHER INFORMATION: Light chain variable domain of anti-albumin
      antibody (ds)

<400> SEQUENCE: 4

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys Arg Thr
            100                 105                 110

<210> SEQ ID NO 5
<211> LENGTH: 16
<212> TYPE: PRT
<213> ORGANISM: Artificial
<220> FEATURE:
<223> OTHER INFORMATION: Linker 1

<400> SEQUENCE: 5

Ser Gly Gly Gly Gly Ser Gly Gly Gly Gly Thr Gly Gly Gly Gly Ser
1               5                   10                  15

<210> SEQ ID NO 6
<211> LENGTH: 15
<212> TYPE: PRT
<213> ORGANISM: Artificial
<220> FEATURE:
<223> OTHER INFORMATION: Linker 2

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 357

<212> TYPE: PRT
<213> ORGANISM: Artificial
<220> FEATURE:
<223> OTHER INFORMATION: A26 Fab Heavy-(G4S,G4T,G4S)-645dsFv(gH5)

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Thr Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Asn Ser Lys Asn Thr Val Tyr Leu Gln Met Asn Ser
305                 310                 315                 320

Leu Arg Ala Glu Asp Thr Ala Val Tyr Tyr Cys Ala Arg Thr Val Pro
                325                 330                 335

Gly Tyr Ser Thr Ala Pro Tyr Phe Asp Leu Trp Gly Gln Gly Thr Leu
            340                 345                 350

Val Thr Val Ser Ser
        355

<210> SEQ ID NO 8
<211> LENGTH: 341

```
<212> TYPE: PRT
<213> ORGANISM: Artificial
<220> FEATURE:
<223> OTHER INFORMATION: A26 Fab Light-(3xG4S)-645dsFv(gL4)

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Asp Ile Gln Met Thr Gln Ser Pro Ser Ser Val
225                 230                 235                 240

Ser Ala Ser Val Gly Asp Arg Val Thr Ile Thr Cys Gln Ser Ser Pro
                245                 250                 255

Ser Val Trp Ser Asn Phe Leu Ser Trp Tyr Gln Gln Lys Pro Gly Lys
            260                 265                 270

Ala Pro Lys Leu Leu Ile Tyr Glu Ala Ser Lys Leu Thr Ser Gly Val
        275                 280                 285

Pro Ser Arg Phe Ser Gly Ser Gly Ser Gly Thr Asp Phe Thr Leu Thr
    290                 295                 300

Ile Ser Ser Leu Gln Pro Glu Asp Phe Ala Thr Tyr Tyr Cys Gly Gly
305                 310                 315                 320

Gly Tyr Ser Ser Ile Ser Asp Thr Thr Phe Gly Cys Gly Thr Lys Val
                325                 330                 335

Glu Ile Lys Arg Thr
            340

<210> SEQ ID NO 9
<211> LENGTH: 119
<212> TYPE: PRT
<213> ORGANISM: Artificial
<220> FEATURE:
```

<223> OTHER INFORMATION: 645gH1 heavy chain variable domain

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Ser Thr Thr Val Tyr Leu Gln Met
65                  70                  75                  80

Asn Ser Leu Arg Ala Glu Asp Thr Ala Val Tyr Tyr Cys Ala Arg Thr
                85                  90                  95

Val Pro Gly Tyr Ser Thr Ala Pro Tyr Phe Asp Leu Trp Gly Gln Gly
            100                 105                 110

Thr Leu Val Thr Val Ser Ser
        115

<210> SEQ ID NO 10
<211> LENGTH: 110
<212> TYPE: PRT
<213> ORGANISM: Artificial
<220> FEATURE:
<223> OTHER INFORMATION: 645gL1 light chain variable domain

<400> SEQUENCE: 10

Asp Ile Val Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Lys
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys
            100                 105                 110

<210> SEQ ID NO 11
<211> LENGTH: 355
<212> TYPE: PRT
<213> ORGANISM: Artificial
<220> FEATURE:
<223> OTHER INFORMATION: A26 Fab Heavy-( 3xG4S)-645dsFv(gH1)

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val

```
            50                  55                  60
Lys Gly Arg Phe Thr Ile Ser Arg Asp Asp Ala Lys Asn Ser Pro Tyr
 65                  70                  75                  80

Leu Gln Met Asn Ser Leu Arg Ala Glu Asp Thr Ala Val Tyr Tyr Cys
                 85                  90                  95

Ala Thr Gly Gly Glu Gly Ile Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Ser Gly Gly Gly
            210                 215                 220

Gly Ser Gly Gly Gly Gly Ser Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
                260                 265                 270

Val Arg Gln Ala Pro Gly Lys Cys Leu Glu Trp Ile Gly Ile Ile Trp
            275                 280                 285

Ala Ser Gly Thr Thr Phe Tyr Ala Thr Trp Ala Lys Gly Arg Phe Thr
            290                 295                 300

Ile Ser Arg Asp Ser Thr Thr Val Tyr Leu Gln Met Asn Ser Leu Arg
305                 310                 315                 320

Ala Glu Asp Thr Ala Val Tyr Tyr Cys Ala Arg Thr Val Pro Gly Tyr
                325                 330                 335

Ser Thr Ala Pro Tyr Phe Asp Leu Trp Gly Gln Gly Thr Leu Val Thr
                340                 345                 350

Val Ser Ser
        355

<210> SEQ ID NO 12
<211> LENGTH: 340
<212> TYPE: PRT
<213> ORGANISM: Artificial
<220> FEATURE:
<223> OTHER INFORMATION: A26 Fab Light-(3xG4S)-645dsFv(gL1)

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Arg Ala Thr Gln Ser Ile Tyr Asn Ala
                20                  25                  30

Leu Ala Trp Tyr Gln Gln Lys Pro Gly Lys Ala Pro Lys Leu Leu Ile
            35                  40                  45

Tyr Asn Ala Asn Thr Leu His Thr Gly Val Pro Ser Arg Phe Ser Ala
```

```
                    50                  55                  60
Ser Gly Ser Gly Thr Asp Ser Thr Leu Thr Ile Ser Ser Leu Gln Pro
 65                      70                  75                  80

Glu Asp Phe Ala Thr Tyr Tyr Cys Gln Gln Tyr Tyr Asp Tyr Pro Leu
                     85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Ser Gly Gly Gly Ser Gly Gly Gly
210                 215                 220

Ser Gly Gly Gly Ser Asp Ile Val Met Thr Gln Ser Pro Ser Ser
225                 230                 235                 240

Val Ser Ala Ser Val Gly Asp Arg Val Thr Ile Thr Cys Gln Ser Ser
                245                 250                 255

Pro Ser Val Trp Ser Asn Phe Leu Ser Trp Tyr Gln Gln Lys Pro Gly
                260                 265                 270

Lys Ala Pro Lys Leu Leu Ile Tyr Glu Ala Ser Lys Leu Thr Ser Gly
            275                 280                 285

Val Pro Ser Arg Phe Lys Gly Ser Gly Ser Gly Thr Asp Phe Thr Leu
290                 295                 300

Thr Ile Ser Ser Leu Gln Pro Glu Asp Phe Ala Thr Tyr Tyr Cys Gly
305                 310                 315                 320

Gly Gly Tyr Ser Ser Ile Ser Asp Thr Thr Phe Gly Cys Gly Thr Lys
                325                 330                 335

Val Glu Ile Lys
            340

<210> SEQ ID NO 13
<211> LENGTH: 789
<212> TYPE: DNA
<213> ORGANISM: Artificial
<220> FEATURE:
<223> OTHER INFORMATION: 645 gH5gL4

<400> SEQUENCE: 13
gaggttcagc tgctggagtc tgagggcggg cttgtccagc ctggagggag cctgcgtctc      60
tcttgtgcag taagcggcat cgacctgtcc aactacgcga ttaactgggt acgtcaggca     120
ccgggtaaag gtctgaatg gatcggcatc atctgggcct ctggtacgac cttctacgct     180
acttgggcca aggtcgtttt caccatctcc cgtgacaact ctaaaaacac cgtgtacctg     240
cagatgaact ctctgcgtgc ggaagacact gcggtttact attgcgcgcg taccgttccg     300
ggctattcta ctgcaccgta cttcgacctg tggggtcagg gtactctggt accgtctcg      360 agtggaggtg gcggttctgg cggtggcggt tccggtggcg gtggatcggg aggtggcggt     420
```

```
tctgatatcc agatgaccca gagtccaagc agtgtttccg ccagcgtagg cgatcgtgtg    480
actattacct gtcagtcctc tccgagcgtt tggtccaact tcctgagctg gtaccagcag    540
aaaccgggta agccccgaa actgctgatc tacgaggcgt ctaaactgac ctctggtgta    600
ccgtcccgtt tctctggctc tggctctggt acggacttca ctctgaccat ctcctctctg    660
cagccggaag actttgcaac gtactactgc ggtggtggtt actcttccat ctctgacacc    720
acgttcggtg aggcaccaa agttgaaatc aaacgtacgc atcaccatca ccatcaccat    780
caccatcac                                                            789
```

```
<210> SEQ ID NO 14
<211> LENGTH: 263
<212> TYPE: PRT
<213> ORGANISM: Artificial
<220> FEATURE:
<223> OTHER INFORMATION: 645 gH5gL4

<400> SEQUENCE: 14
```

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Gly Tyr Ser Ser Ile Ser Asp Thr
225                 230                 235                 240

Thr Phe Gly Gly Gly Thr Lys Val Glu Ile Lys Arg Thr His His His
                245                 250                 255

His His His His His
            260

```
<210> SEQ ID NO 15
<211> LENGTH: 789
```

<212> TYPE: DNA
<213> ORGANISM: Artificial
<220> FEATURE:
<223> OTHER INFORMATION: 645 gH5gL4ds

<400> SEQUENCE: 15

```
gaggttcagc tgctggagtc tggaggcggg cttgtccagc ctggagggag cctgcgtctc     60
tcttgtgcag taagcggcat cgacctgtcc aactacgcga ttaactgggt acgtcaggca    120
ccgggtaaat gcctggaatg gatcggcatc atctgggcct ctggtacgac cttctacgct    180
acttgggcca aggtcgttt caccatctcc cgtgacaact ctaaaaacac cgtgtacctg    240
cagatgaact ctctgcgtgc ggaagacact gcggtttact attgcgcgcg taccgttccg    300
ggctattcta ctgcaccgta cttcgacctg tggggtcagg gtactctggt accgtctcg    360
agtggaggtg gcggttctgg cggtggcggt tccggtggcg gtggatcggg aggtggcggt    420
tctgatatcc agatgaccca gagtccaagc agtgtttccg ccagcgtagg cgatcgtgtg    480
actattacct gtcagtcctc tccgagcgtt tggtccaact tcctgagctg gtaccagcag    540
aaaccgggta agccccgaaa actgctgatc tacgaggcgt ctaaactgac ctctggtgta    600
ccgtcccgtt tctctggctc tggctctggt acggacttca ctctgaccat ctcctctctg    660
cagccggaag actttgcaac gtactactgc ggtggtggtt actcttccat ctctgacacc    720
acgttcggtt gtggcaccaa agttgaaatc aaacgtacgc atcaccatca ccatcaccat    780
caccatcac                                                           789
```

<210> SEQ ID NO 16
<211> LENGTH: 263
<212> TYPE: PRT
<213> ORGANISM: Artificial
<220> FEATURE:
<223> OTHER INFORMATION: 645 gH5gL4ds

<400> SEQUENCE: 16

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Ar

```
                  180                 185                 190
Ala Ser Lys Leu Thr Ser Gly Val Pro Ser Arg Phe Ser Gly Ser Gly
            195                 200                 205

Ser Gly Thr Asp Phe Thr Leu Thr Ile Ser Ser Leu Gln Pro Glu Asp
        210                 215                 220

Phe Ala Thr Tyr Tyr Cys Gly Gly Gly Tyr Ser Ser Ile Ser Asp Thr
225                 230                 235                 240

Thr Phe Gly Cys Gly Thr Lys Val Glu Ile Lys Arg Thr His His His
                245                 250                 255

His His His His His His His
            260

<210> SEQ ID NO 17
<211> LENGTH: 20
<212> TYPE: PRT
<213> ORGANISM: Artificial
<220> FEATURE:
<223> OTHER INFORMATION: Linker

<400> SEQUENCE: 17

Gly Gly Gly Gly Ser Gly Gly Gly Ser Gly Gly Gly Gly Ser Gly
1               5                   10                  15

Gly Gly Gly Ser
            20

<210> SEQ ID NO 18
<211> LENGTH: 16
<212> TYPE: PRT
<213> ORGANISM: Artificial
<220> FEATURE:
<223> OTHER INFORMATION: Linker

<400> SEQUENCE: 18

Ser Gly Gly Gly Gly Ser Gly Gly Gly Gly Ser Gly Gly Gly Gly Ser
1               5                   10                  15

<210> SEQ ID NO 19
<211> LENGTH: 105
<212> TYPE: PRT
<213> ORGANISM: Artificial
<220> FEATURE:
<223> OTHER INFORMATION: cKappa

<400> SEQUENCE: 19

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 20
```

```
<211> LENGTH: 103
<212> TYPE: PRT
<213> ORGANISM: Artificial
<220> FEATURE:
<223> OTHER INFORMATION: CH1

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 21
<211> LENGTH: 7
<212> TYPE: PRT
<213> ORGANISM: Artificial
<220> FEATURE:
<223> OTHER INFORMATION: Linker

<400> SEQUENCE: 21

Ser Gly Gly Gly Gly Ser Glu
1               5

<210> SEQ ID NO 22
<211> LENGTH: 6
<212> TYPE: PRT
<213> ORGANISM: Artificial
<220> FEATURE:
<223> OTHER INFORMATION: Linker

<400> SEQUENCE: 22

Asp Lys Thr His Thr Ser
1               5

<210> SEQ ID NO 23
<211> LENGTH: 5
<212> TYPE: PRT
<213> ORGANISM: Artificial
<220> FEATURE:
<223> OTHER INFORMATION: Linker

<400> SEQUENCE: 23

Gly Gly Gly Gly Ser
1               5

<210> SEQ ID NO 24
<211> LENGTH: 10
<212> TYPE: PRT
<213> ORGANISM: Artificial
<220> FEATURE:
<223> OTHER INFORMATION: Linker

<400> SEQUENCE: 24

Gly Gly Gly Gly Ser Gly Gly Gly Gly Ser
```

-continued

```
1               5                   10

<210> SEQ ID NO 25
<211> LENGTH: 15
<212> TYPE: PRT
<213> ORGANISM: Artificial
<220> FEATURE:
<223> OTHER INFORMATION: Linker

<400> SEQUENCE: 25

Gly Gly Gly Gly Ser Gly Gly Gly Gly Ser Gly Gly Gly Gly Ser
1               5                   10                  15

<210> SEQ ID NO 26
<211> LENGTH: 21
<212> TYPE: PRT
<213> ORGANISM: Artificial
<220> FEATURE:
<223> OTHER INFORMATION: Linker

<400> SEQUENCE: 26

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 27
<211> LENGTH: 25
<212> TYPE: PRT
<213> ORGANISM: Artificial
<220> FEATURE:
<223> OTHER INFORMATION: Linker

<400> SEQUENCE: 27

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 28
<211> LENGTH: 11
<212> TYPE: PRT
<213> ORGANISM: Artificial
<220> FEATURE:
<223> OTHER INFORMATION: Linker

<400> SEQUENCE: 28

Ala Ala Ala Gly Ser Gly Gly Ala Ser Ala Ser
1               5                   10

<210> SEQ ID NO 29
<211> LENGTH: 16
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 29

Ala Ala Ala Gly Ser Gly Xaa Gly Gly Gly Ser Gly Ala Ser Ala Ser
1               5                   10                  15

<210> SEQ ID NO 30
```

```
<211> LENGTH: 21
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 30

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 31
<211> LENGTH: 26
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 31

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 32
<211> LENGTH: 31
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 32

Ala Ala Ala Gly Ser Gly Xaa Gly Gly Gly Ser Xaa Gly Gly Gly Ser
1               5                   10                  15
```

Xaa Gly Gly Gly Ser Xaa Gly Gly Ser Gly Ala Ser Ala Ser
            20                  25                  30

<210> SEQ ID NO 33
<211> LENGTH: 13
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 33

Ala Ala Ala Gly Ser Gly Xaa Ser Gly Ala Ser Ala Ser
1               5                   10

<210> SEQ ID NO 34
<211> LENGTH: 56
<212> TYPE: PRT
<213> ORGANISM: Artificial
<220> FEATURE:
<223> OTHER INFORMATION: Linker

<400> SEQUENCE: 34

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr Pro Gly Gly Asn
            20                  25                  30

Arg Gly Thr Thr Thr Thr Arg Arg Pro Ala Thr Thr Thr Gly Ser Ser
        35                  40                  45

Pro Gly Pro Thr Gln Ser His Tyr
    50                  55

<210> SEQ ID NO 35
<211> LENGTH: 11
<212> TYPE: PRT
<213> ORGANISM: Artificial
<220> FEATURE:
<223> OTHER INFORMATION: Linker

<400> SEQUENCE: 35

Ala Thr Thr Thr Gly Ser Ser Pro Gly Pro Thr
1               5                   10

<210> SEQ ID NO 36
<211> LENGTH: 6
<212> TYPE: PRT
<213> ORGANISM: Artificial
<220> FEATURE:
<223> OTHER INFORMATION: Linker

<400> SEQUENCE: 36

Ala Thr Thr Thr Gly Ser
1               5

<210> SEQ ID NO 37
<211> LENGTH: 21
<212> TYPE: PRT
<213> ORGANISM: Artificial
<220> FEATURE:
<223> OTHER INFORMATION: Linker

<400> SEQUENCE: 37

Glu Pro Ser Gly Pro Ile Ser Thr Ile Asn Ser Pro Pro Ser Lys Glu

Ser His Lys Ser Pro
            20

<210> SEQ ID NO 38
<211> LENGTH: 15
<212> TYPE: PRT
<213> ORGANISM: Artificial
<220> FEATURE:
<223> OTHER INFORMATION: Linker

<400> SEQUENCE: 38

Gly Thr Val Ala Ala Pro Ser Val Phe Ile Phe Pro Pro Ser Asp
1               5                   10                  15

<210> SEQ ID NO 39
<211> LENGTH: 15
<212> TYPE: PRT
<213> ORGANISM: Artificial
<220> FEATURE:
<223> OTHER INFORMATION: Linker

<400> SEQUENCE: 39

Gly Gly Gly Gly Ile Ala Pro Ser Met Val Gly Gly Gly Gly Ser
1               5                   10                  15

<210> SEQ ID NO 40
<211> LENGTH: 15
<212> TYPE: PRT
<213> ORGANISM: Artificial
<220> FEATURE:
<223> OTHER INFORMATION: Linker

<400> SEQUENCE: 40

Gly Gly Gly Gly Lys Val Glu Gly Ala Gly Gly Gly Gly Gly Ser
1               5                   10                  15

<210> SEQ ID NO 41
<211> LENGTH: 15
<212> TYPE: PRT
<213> ORGANISM: Artificial
<220> FEATURE:
<223> OTHER INFORMATION: Linker

<400> SEQUENCE: 41

Gly Gly Gly Gly Ser Met Lys Ser His Asp Gly Gly Gly Gly Ser
1               5                   10                  15

<210> SEQ ID NO 42
<211> LENGTH: 15
<212> TYPE: PRT
<213> ORGANISM: Artificial
<220> FEATURE:
<223> OTHER INFORMATION: Linker

<400> SEQUENCE: 42

Gly Gly Gly Gly Asn Leu Ile Thr Ile Val Gly Gly Gly Gly Ser
1               5                   10                  15

<210> SEQ ID NO 43
<211> LENGTH: 15
<212> TYPE: PRT
<213> ORGANISM: Artificial
<220> FEATURE:
<223> OTHER INFORMATION: Linker

<400> SEQUENCE: 43

```
Gly Gly Gly Gly Val Val Pro Ser Leu Pro Gly Gly Gly Gly Ser
1               5                   10                  15
```

<210> SEQ ID NO 44
<211> LENGTH: 12
<212> TYPE: PRT
<213> ORGANISM: Artificial
<220> FEATURE:
<223> OTHER INFORMATION: Linker

<400> SEQUENCE: 44

```
Gly Gly Glu Lys Ser Ile Pro Gly Gly Gly Ser
1               5                   10
```

<210> SEQ ID NO 45
<211> LENGTH: 18
<212> TYPE: PRT
<213> ORGANISM: Artificial
<220> FEATURE:
<223> OTHER INFORMATION: Linker

<400> SEQUENCE: 45

```
Arg Pro Leu Ser Tyr Arg Pro Pro Phe Pro Phe Gly Phe Pro Ser Val
1               5                   10                  15

Arg Pro
```

<210> SEQ ID NO 46
<211> LENGTH: 18
<212> TYPE: PRT
<213> ORGANISM: Artificial
<220> FEATURE:
<223> OTHER INFORMATION: Linker

<400> SEQUENCE: 46

```
Tyr Pro Arg Ser Ile Tyr Ile Arg Arg His Pro Ser Pro Ser Leu
1               5                   10                  15

Thr Thr
```

<210> SEQ ID NO 47
<211> LENGTH: 18
<212> TYPE: PRT
<213> ORGANISM: Artificial
<220> FEATURE:
<223> OTHER INFORMATION: Linker

<400> SEQUENCE: 47

```
Thr Pro Ser His Leu Ser His Ile Leu Pro Ser Phe Gly Leu Pro Thr
1               5                   10                  15

Phe Asn
```

<210> SEQ ID NO 48
<211> LENGTH: 18
<212> TYPE: PRT
<213> ORGANISM: Artificial
<220> FEATURE:
<223> OTHER INFORMATION: Linker

<400> SEQUENCE: 48

```
Arg Pro Val Ser Pro Phe Thr Phe Pro Arg Leu Ser Asn Ser Trp Leu
1               5                   10                  15

Pro Ala
```

<210> SEQ ID NO 49

```
<211> LENGTH: 18
<212> TYPE: PRT
<213> ORGANISM: Artificial
<220> FEATURE:
<223> OTHER INFORMATION: Linker

<400> SEQUENCE: 49

Ser Pro Ala Ala His Phe Pro Arg Ser Ile Pro Arg Pro Gly Pro Ile
1               5                   10                  15

Arg Thr

<210> SEQ ID NO 50
<211> LENGTH: 18
<212> TYPE: PRT
<213> ORGANISM: Artificial
<220> FEATURE:
<223> OTHER INFORMATION: Linker

<400> SEQUENCE: 50

Ala Pro Gly Pro Ser Ala Pro Ser His Arg Ser Leu Pro Ser Arg Ala
1               5                   10                  15

Phe Gly

<210> SEQ ID NO 51
<211> LENGTH: 18
<212> TYPE: PRT
<213> ORGANISM: Artificial
<220> FEATURE:
<223> OTHER INFORMATION: Linker

<400> SEQUENCE: 51

Pro Arg Asn Ser Ile His Phe Leu His Pro Leu Leu Val Ala Pro Leu
1               5                   10                  15

Gly Ala

<210> SEQ ID NO 52
<211> LENGTH: 18
<212> TYPE: PRT
<213> ORGANISM: Artificial
<220> FEATURE:
<223> OTHER INFORMATION: Linker

<400> SEQUENCE: 52

Met Pro Ser Leu Ser Gly Val Leu Gln Val Arg Tyr Leu Ser Pro Pro
1               5                   10                  15

Asp Leu

<210> SEQ ID NO 53
<211> LENGTH: 18
<212> TYPE: PRT
<213> ORGANISM: Artificial
<220> FEATURE:
<223> OTHER INFORMATION: Linker

<400> SEQUENCE: 53

Ser Pro Gln Tyr Pro Ser Pro Leu Thr Leu Thr Leu Pro Pro His Pro
1               5                   10                  15

Ser Leu

<210> SEQ ID NO 54
<211> LENGTH: 18
<212> TYPE: PRT
<213> ORGANISM: Artificial
<220> FEATURE:
```

<223> OTHER INFORMATION: Linker

<400> SEQUENCE: 54

Asn Pro Ser Leu Asn Pro Pro Ser Tyr Leu His Arg Ala Pro Ser Arg
1               5                   10                  15

Ile Ser

<210> SEQ ID NO 55
<211> LENGTH: 17
<212> TYPE: PRT
<213> ORGANISM: Artificial
<220> FEATURE:
<223> OTHER INFORMATION: Linker

<400> SEQUENCE: 55

Leu Pro Trp Arg Thr Ser Leu Leu Pro Ser Leu Pro Leu Arg Arg Arg
1               5                   10                  15

Pro

<210> SEQ ID NO 56
<211> LENGTH: 18
<212> TYPE: PRT
<213> ORGANISM: Artificial
<220> FEATURE:
<223> OTHER INFORMATION: Linker

<400> SEQUENCE: 56

Pro Pro Leu Phe Ala Lys Gly Pro Val Gly Leu Leu Ser Arg Ser Phe
1               5                   10                  15

Pro Pro

<210> SEQ ID NO 57
<211> LENGTH: 18
<212> TYPE: PRT
<213> ORGANISM: Artificial
<220> FEATURE:
<223> OTHER INFORMATION: Linker

<400> SEQUENCE: 57

Val Pro Pro Ala Pro Val Val Ser Leu Arg Ser Ala His Ala Arg Pro
1               5                   10                  15

Pro Tyr

<210> SEQ ID NO 58
<211> LENGTH: 17
<212> TYPE: PRT
<213> ORGANISM: Artificial
<220> FEATURE:
<223> OTHER INFORMATION: Linker

<400> SEQUENCE: 58

Leu Arg Pro Thr Pro Pro Arg Val Arg Ser Tyr Thr Cys Cys Pro Thr
1               5                   10                  15

Pro

<210> SEQ ID NO 59
<211> LENGTH: 18
<212> TYPE: PRT
<213> ORGANISM: Artificial
<220> FEATURE:
<223> OTHER INFORMATION: Linker

<400> SEQUENCE: 59

Pro Asn Val Ala His Val Leu Pro Leu Leu Thr Val Pro Trp Asp Asn
1               5                   10                  15

Leu Arg

<210> SEQ ID NO 60
<211> LENGTH: 18
<212> TYPE: PRT
<213> ORGANISM: Artificial
<220> FEATURE:
<223> OTHER INFORMATION: Linker

<400> SEQUENCE: 60

Cys Asn Pro Leu Leu Pro Leu Cys Ala Arg Ser Pro Ala Val Arg Thr
1               5                   10                  15

Phe Pro

<210> SEQ ID NO 61
<211> LENGTH: 11
<212> TYPE: PRT
<213> ORGANISM: Artificial
<220> FEATURE:
<223> OTHER INFORMATION: Linker

<400> SEQUENCE: 61

Gly Ala Pro Ala Pro Ala Ala Pro Ala Pro Ala
1               5                   10

<210> SEQ ID NO 62
<211> LENGTH: 4
<212> TYPE: PRT
<213> ORGANISM: Artificial
<220> FEATURE:
<223> OTHER INFORMATION: Linker

<400> SEQUENCE: 62

Pro Pro Pro Pro
1

<210> SEQ ID NO 63
<211> LENGTH: 8
<212> TYPE: PRT
<213> ORGANISM: Artificial
<220> FEATURE:
<223> OTHER INFORMATION: Linker

<400> SEQUENCE: 63

Asp Lys Thr His Thr Cys Ala Ala
1               5

<210> SEQ ID NO 64
<211> LENGTH: 11
<212> TYPE: PRT
<213> ORGANISM: Artificial
<220> FEATURE:
<223> OTHER INFORMATION: Linker

<400> SEQUENCE: 64

Asp Lys Thr His Thr Cys Pro Pro Cys Pro Ala
1               5                   10

<210> SEQ ID NO 65
<211> LENGTH: 18
<212> TYPE: PRT
<213> ORGANISM: Artificial
<220> FEATURE:
<223> OTHER INFORMATION: Linker

<400> SEQUENCE: 65

Asp Lys Thr His Thr Cys Pro Pro Cys Pro Ala Thr Cys Pro Pro Cys
1               5                   10                  15

Pro Ala

<210> SEQ ID NO 66
<211> LENGTH: 25
<212> TYPE: PRT
<213> ORGANISM: Artificial
<220> FEATURE:
<223> OTHER INFORMATION: Linker

<400> SEQUENCE: 66

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 67
<211> LENGTH: 30
<212> TYPE: PRT
<213> ORGANISM: Artificial
<220> FEATURE:
<223> OTHER INFORMATION: Linker

<400> SEQUENCE: 67

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 68
<211> LENGTH: 31
<212> TYPE: PRT
<213> ORGANISM: Artificial
<220> FEATURE:
<223> OTHER INFORMATION: Linker

<400> SEQUENCE: 68

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 69
<211> LENGTH: 15
<212> TYPE: PRT
<213> ORGANISM: Artificial
<220> FEATURE:
<223> OTHER INFORMATION: Linker

<400> SEQUENCE: 69

Asp Lys Thr His Thr Cys Cys Val Glu Cys Pro Pro Cys Pro Ala
1               5                   10                  15

<210> SEQ ID NO 70
<211> LENGTH: 26
<212> TYPE: PRT
<213> ORGANISM: Artificial
<220> FEATURE:
<223> OTHER INFORMATION: Linker

<400> SEQUENCE: 70

```
Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20              25

<210> SEQ ID NO 71
<211> LENGTH: 11
<212> TYPE: PRT
<213> ORGANISM: Artificial
<220> FEATURE:
<223> OTHER INFORMATION: Linker

<400> SEQUENCE: 71

Asp Lys Thr His Thr Cys Pro Ser Cys Pro Ala
1               5                   10
```